(12) United States Patent
Myers et al.

(10) Patent No.: US 8,936,825 B2
(45) Date of Patent: Jan. 20, 2015

(54) METHOD AND SYSTEM FOR FORMING A PHARMACEUTICAL PRODUCT DIRECTLY ONTO A PACKAGING SURFACE

(75) Inventors: Garry L. Myers, Kingsport, TN (US); Beuford A. Bogue, New Carlisle, IN (US); Greg Slominski, Valparaiso, IN (US); Kevin Davidson, Valparaiso, IN (US); Laura Miloshoff, Schereville, IN (US)

(73) Assignee: Monosol RX, LLC, Warren, NJ (US)

( * ) Notice: Subject to any disclaimer, the term of this patent is extended or adjusted under 35 U.S.C. 154(b) by 0 days.

(21) Appl. No.: 13/238,024

(22) Filed: Sep. 21, 2011

(65) Prior Publication Data

US 2012/0076921 A1     Mar. 29, 2012

Related U.S. Application Data

(60) Provisional application No. 61/385,758, filed on Sep. 23, 2010.

(51) Int. Cl.
*A61K 9/70* (2006.01)
*B05D 3/02* (2006.01)

(52) U.S. Cl.
CPC .................................. *A61K 9/7007* (2013.01)
USPC ......... 427/2.14; 427/2.31; 424/443; 424/484; 424/486

(58) Field of Classification Search
CPC ... A61K 9/703; A61K 9/0014; A61K 9/7015; A61K 15/001
USPC ................. 424/443, 484, 486; 427/2.14, 2.31
See application file for complete search history.

(56) References Cited

U.S. PATENT DOCUMENTS

| | | | | |
|---|---|---|---|---|
| 4,128,445 | A * | 12/1978 | Sturzenegger et al. | 156/64 |
| 4,305,502 | A * | 12/1981 | Gregory et al. | 206/532 |
| 4,797,284 | A * | 1/1989 | Loper et al. | 424/449 |
| 4,925,670 | A * | 5/1990 | Schmidt | 424/443 |
| 5,188,838 | A * | 2/1993 | Deleuil et al. | 424/451 |
| 6,059,913 | A * | 5/2000 | Asmussen et al. | 156/230 |
| 6,238,700 | B1 * | 5/2001 | Dohner et al. | 424/484 |
| 6,682,757 | B1 * | 1/2004 | Wright | 424/448 |
| 7,993,674 | B2 | 8/2011 | Weibel | |
| 2003/0224044 | A1 * | 12/2003 | Weibel | 424/465 |
| 2004/0241242 | A1 * | 12/2004 | Fuisz et al. | 424/486 |
| 2007/0169878 | A1 * | 7/2007 | Tucker et al. | 156/220 |

OTHER PUBLICATIONS

International Search Report PCT/US2011/052450 Dated Jan. 27, 2012.
Written Opinion PCT/US2011/052450 Dated Jan. 27, 2012.

* cited by examiner

*Primary Examiner* — Cachet Sellman
(74) *Attorney, Agent, or Firm* — Hoffmann & Baron, LLP

(57) ABSTRACT

The present invention relates to a method for forming a pharmaceutical product, such as a dissolvable film dosage form, onto a surface. Particularly, the present invention relates to a method of forming a pharmaceutical product directly onto the surface of a substrate.

87 Claims, 9 Drawing Sheets

US 8,936,825 B2

METHOD AND SYSTEM FOR FORMING A PHARMACEUTICAL PRODUCT DIRECTLY ONTO A PACKAGING SURFACE

CROSS-REFERENCE TO RELATED APPLICATIONS

The present invention claims the benefit of priority to U.S. Provisional Application No. 61/385,758, filed Sep. 23, 2010, the entire contents of which are incorporated by reference herein.

FIELD OF THE INVENTION

The present invention relates to a method for forming a pharmaceutical product, such as a dissolvable film dosage form, onto a surface. Particularly, the present invention relates to a method of forming a pharmaceutical product directly onto the surface of a packaging material.

BACKGROUND OF THE INVENTION

When film dosages are manufactured, particularly self-supporting film dosages, the film is generally formed in the form of a continuous sheet or web or material, which must then be cut into individual dosages. There is inherent scrap, or wasted material, associated with the manufacturing and processing steps. This scrap results in unusable material that is simply discarded. When such wasted material includes precious matter such as active drugs and pharmaceuticals, this wasted material can be extremely expensive.

It is desirable to solve the present problems associated with the art to yield a more efficient manufacturing and packaging process to form individual film doses, especially those containing an active component. Further, it is a desired aspect of the present invention to provide a method for manufacturing individual film dosages directly onto the surface of a package, where the package may be sealed and may form a housing for the individual film dosage.

SUMMARY OF THE INVENTION

In one embodiment of the present invention there is provided a method of forming an individual film dosage, including the steps of: preparing a film forming matrix; providing a substrate having a top surface; depositing a pre-determined amount of the matrix onto the top surface of the substrate to form a wet film forming product; drying the wet film forming product to form a dried film product; and placing a sealing layer on the top surface of the substrate, where the sealing layer effectively seals the dried film product between the sealing layer and the substrate.

In another embodiment of the present invention, there is provided a method of forming an individual film dosage, including the steps of: preparing a film forming matrix including at least one water soluble polymer; providing a substrate having at least one top surface; depositing a pre-determined amount of the film forming matrix onto the top surface of the substrate to form a wet film forming product; drying the wet film forming product to form a dried film product; storing the dried film product for a pre-determined length of time; and placing a sealing layer on the top surface of the substrate, where the sealing layer effectively seals the dried film product between the sealing layer and the substrate.

The present invention with its various embodiments may be better understood through a study of the following figures and description.

DETAILED DESCRIPTION OF THE PREFERRED EMBODIMENTS

Figure 1:
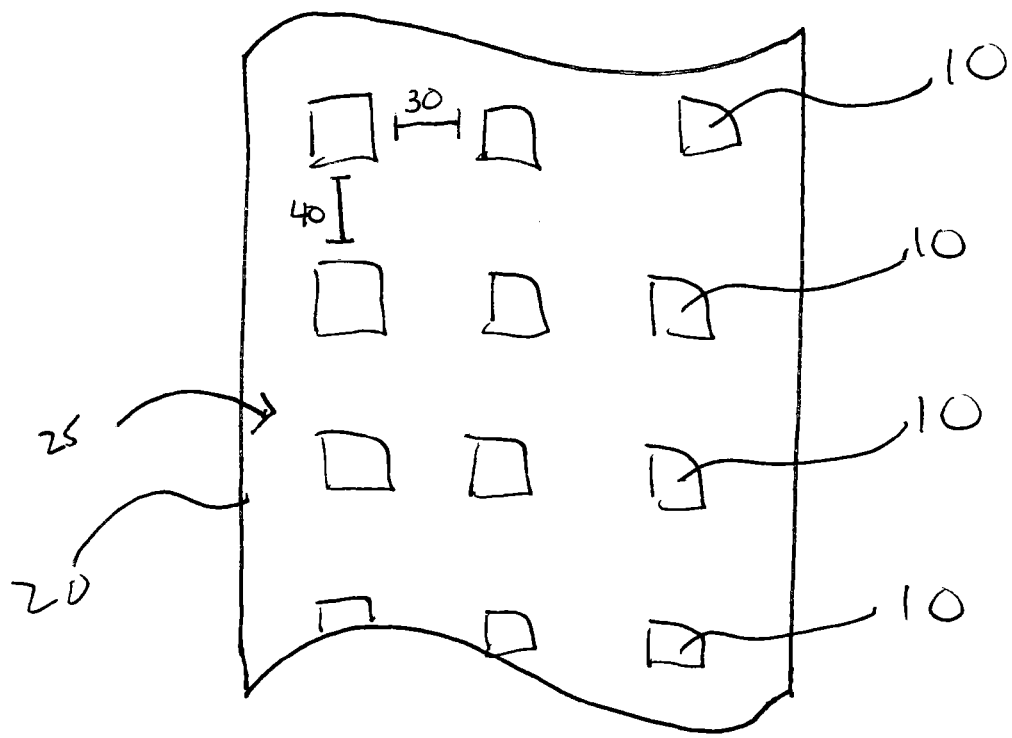
FIG. 1 depicts a plurality of individual wet film products deposited onto the surface of a substrate.

The present invention relates to methods and apparatuses designed for forming film products, including film products that include at least one active composition. Specifically, the invention relates to methods of forming film products on a substrate, while maintaining the uniformity of content and the structural integrity of the individual film product. Further, the invention provides a method and apparatus for forming film products that minimizes the amount of waste typically required in film processing. Film systems embody a field of technology that has major advantages in areas of administering drug, medicament, and various other active and agent delivery systems to an individual in need thereof. In order to provide a desirable final product that exhibits advantageous characteristics and desirable properties, including uniformity of content, the processing and manufacturing of film strips and film technology is technologically demanding and cumbersome.

As used herein, the terms "pharmaceutical", "medicament", "drug" and "active" may be used interchangeably, and refer to a substance or composition useful for the prevention or treatment of a condition. The terms may include therapeutic actives, pharmaceuticals, neutraceuticals, cosmetic agents, biologic agents, bioeffective substances, and the like.

It will be understood that the term "film" includes delivery systems of any thickness, including films and film strips, sheets, discs, wafers, and the like, in any shape, including rectangular, square, or other desired shape. The film may be in the form of a continuous roll of film or may be sized to a desired length and width. The films described herein may be any desired thickness and size suitable for the intended use. For example, a film of the present invention may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. In addition, the term "film" includes single-layer compositions as well as multi-layer compositions, such as laminated films, coatings on films and the like. The composition in its dried film form maintains a uniform distribution of components through the application of controlled drying of the film. Films may include a pouch or region of medicament between two films.

The term "patch" as used herein is intended to include multi-layered film products, where the first layer (or "backing layer") is a film product that has a slower rate of dissolution than the second layer (or "active layer"). In some embodiments, the backing layer of a patch may not be a dissolvable material. Patches described herein generally include the first and second layers adhered to each other, where the second layer has a smaller length and/or width of the first layer, such that at least a portion of the surface of the first layer is visible outside of the second layer. In this fashion, the portion of the surface of the first layer that is visible outside of the second layer may be adhered to one or more body surfaces and allow absorption of the active through the body surface.

Films formed by the present invention may be suitable for administration to at least one mucosal region of the body of the user. In some embodiments of the invention, the films are intended for oral administration. In other embodiments, the films are intended for topical administration. As used herein, the term "topical agent" is meant to encompass active agents that are applied to a particular surface area. For example, in one embodiment, a topical agent is applied to an area of the skin. In other embodiments, the topical agent may also be applied to mucosal areas of the body, such as the oral (e.g., buccal, sublingual, tongue), vaginal, ocular and anal areas of the body. In other embodiments, the topical agent may be applied to organs in the body, such as during surgery, and may remain within the body after surgery is completed. Actives in the film may be absorbed through the skin of a user. In other embodiments, a topical agent is applied to a hard surface, such as a particular surface area in need of treatment. In other embodiments, the films of the present invention are ingestible, and are intended to be placed in the mouth of the user and swallowed as the film disintegrates.

The medicament may be dispersed throughout the film, or it may be deposited onto one or more surfaces of the film. In either way, it is desirable that the amount of medicament per unit area is substantially uniform throughout the film. It is desired that the films of the present invention include a uniformity of component distribution throughout the volume of a given film. Such uniformity includes a substantially uniform amount of medicament per unit volume of the film, whether the medicament is within the matrix of the film or coated, laminated, or stabilized on one or more surfaces thereof. When such films are cut into individual units, the amount of the agent in the unit can be known with a great deal of accuracy. For the films formed herein, it is understood by one of ordinary skill in the art that the resulting film is not required to be exactly 100% uniform. All that is required is that the film be "substantially uniform", i.e., a slight amount of non-uniformity is understood to be acceptable. "Substantially uniform" may include, for example, a film that is about 90% uniform in content from one region of the film to another, or a film that is about 95% uniform in content from one region of the film to another, and most desirably about 99% uniform in content from one region of the film to another. In some embodiments, substantially uniform may include about 90 to about 110% variation in the weight of a component from dosage unit to dosage unit, where the mean is the target weight in mg for the particular dosage. For example, in a dosage that is intended to include 10 mg of one component, a uniform dosage would include from about 9 mg to about 11 mg for that component.

It is desirable that any individual film products formed by the present invention be substantially uniform in content with respect to each other. That is, the individual film products formed by the present invention should have approximately the same content composition as each other film product. Of course, it will be understood that some deviation is to be expected during the manufacturing process, but desirably at least 90% of the individual film products should be substantially uniform in content with respect to each other (i.e., there should be no more than 10% variance in active content between films made from the same batch).

Uniformity of medicament throughout the film is important in administering an accurate and effective dose of medicament to a user. Various methods of forming uniform films, as well as various polymers, additives and fillers, may be used, including those methods and materials described in U.S. Pat. Nos. 7,425,292, 7,357,891 and 7,666,337, which are herein incorporated by reference in their entireties. Any number of active components or pharmaceutical agents may be included in the films discussed herein. The active component(s) may be disposed within any layer of film products formed herein, may be placed between one or more layers of film, may be placed onto one or more surfaces of the film products, or any combination thereof.

The present invention may use one or more actives in the film products. Any active may be used, including therapeutic agents, bioeffective agents, pharmaceutical agents, or any bioactive agents.

Non-limiting examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (commercially available as Oxycontin®); ibuprofen (commercially available as Motrin®, Advil®, Motrin Children's®, Motrin IBC), Advil Children's®, Motrin Infants'®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP® and Aminofen®), and combinations thereof that may optionally include caffeine. Other pain relieving agents may be used in the present invention, including meperidine hydrochloride (commercially available as Demerol®), capsaicin (commercially available as Qutenza®), morphine sulfate and naltrexone hydrochloride (commercially available as Embeda®), hydromorphone hydrochloride (commercially available as Dilaudid®), propoxyphene napsylate and acetaminophen (commercially available as Darvocet-N®), Fentanyl (commercially available as Duragesic®, Onsolis®, and Fentora®), sodium hyaluronate (commercially avialble as Euflexxa®), adalimumab (commercially available as Humira®), sumatriptan succinate (commercially available as Imitrex®), fentanyl iontophoretic (commercially available as Ionsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The present invention may further include agents such as NSAIDs, including etodolac (commercially available as Lodine®), ketorolac tromethamine (commercially available as Acular® or Acuvail®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), diclofenac potassium (commercially available as Cambia® or Zipsor®), and misoprostol (commercially available as Cytotec®). Opiate agonists and antagonists, such as buprenorphine and naloxone are further examples of drugs for use in the present invention.

Other preferred drugs for other preferred active ingredients for use in the present invention include anti-diarrheals such as loperamide (commercially available as Imodium AD®, Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethophan HBr and phenylephrine HCl (available as Triaminic®) may be included in the film compositions of the present invention.

Other active agents useful in the present invention include, but are not limited to alcohol dependence treatment, such as acamprosate calcium (commercially available as Campral®); Allergy treatment medications, such as promethazine hydrochloride (commercially available as Phenergan®), bepotastine besilate (commercially available as Bepreve®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and antihistamines such as diphenhydramine HCl (available as Benadryl®), loratadine (available as Claritin®), astemizole (available as Hismanal®), nabumetone (available as Relafen®), diphenydramine HCL (available as TheraFlu®) and clemastine (available as Tavist®).

Films of the present invention may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exeloni®), caprylidene (commercially available as Axona®), and memantine (commercially available as Namenda®); anemia medication, such as cyanocobalamin (commercially available as Nascobal®) and ferumoxytol (commercially available as Feraheme®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifensin; anti-Alzheimer's agents, such as nicergoline; and Ca$^H$-antagonists such as nifedipine (commercially available as Procardia® and Adalat®).

Actives useful in the present invention may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); angioedema medication, such as C1 esterase Inhibitor (human) (commercially available as Berinert®) and ecallantide (commercially available as Kalbitor®); and antibacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethylsuccinate/Sulfisoxazole acetyl (commercially available as Pediazole®), and levofloxacin (commercially available as Levaquin®).

The present invention may further include one or more Antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), besifloxacin (commercially available as Besivance®), clarithromycin (commercially available as Biaxin®), ceftibuten (commercially available as Cedax®), cefuroxime axetil (commercially available as Ceftin®), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/S®, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), dexamethasone (commercially available as Ozurdex®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), bevacizumab (commercially available as Avastin®), everolimus (commercially available as Afinitor®), pazopanib (commercially available as Votrient®), and anastrozole (commercially available as Arimidex®); leukemia treatment, such as ofatumumab (commercially available as Arzerra®); anti-thrombotic drugs, such as antithrombin recombinant lyophilized powder (commercially available as Atryn®), prasugrel (commercially available as Efient®); anti-coagulants, such as aspirin with extended-release dipyridamole (commercially available as Aggrenox®), warfarin sodium (commercially available as Coumadin®), dipyridamole (commercially available as Persantine®), dalteparin (commercially available as Fragmin®), danaparoid (commercially available as Orgaran®), enoxaparin (commercially available as Lovenox®), heparin (commercially available as Hep-Lock, Hep-Pak, Hep-Pak CVC, Heparin Lock Flush), tinzaparin (commercially available as Innohep®), and clopidogrel bisulfate (commercially available as Plavix®); antiemetics, such as granisetron hydrochloride (commercially available as Kytril®) and nabilone (commercially available as Cesamet®), trimethobenzamide hydrochloride (commercially available as Tigan®), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Active agents may further include anti-inflammatory medications, such as hydroxychloroquine sulfate (commercially available as Plaquenil®), fluticasone propionate (commercially available as Cutivate®), canakinumab (commercially available as Ilaris®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including timidazole (commercially available as Tindamax®); appetite treatment mediations, such as megestrol acetate (commercially available as Megace ES®), phentermine hydrochloride (commercially available as Adipex-P®), and diethylpropion hydrochloride (commercially available as Tenuate®); arthritis medications, including leflunomide (commercially available as Arava®), certolizumab pegol (commercially available as Cimzia®), diclofenac sodium (commercially available as Pennsaid®), golimumab (commercially available as Simponi®), and tocilizumab (commercially available as Actemra®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan® or Gelnique®), darifenacin (commercially available as Enablex®), and solifenacin succinate (commercially available as VESIcare®); blood vessel constrictors, such as methylergonovine maleate (commercially available as Methergine®); plasma uric managers, such as rasburicase (commercially available as Elitek®); iron deficiency anemia medications, such as ferumoxytol (commercially available as Feraheme®); lymphoma medications, such as pralatrexate (commercially available as Folotyn®), romidepsin (commercially available as Isodax®); malaria medication, such as artemether/lumefantrine (commercially available as Coartem®); hyponatremia medication, such as tolvatpan (commercially available as Samsca®); medication for treatment of von Willebrand disease (commercially available as Wilate®); anti-hypertension medications, such as treprostinil (commercially available as Tyvaso®), tadalafil (commercially available as Adcirca®); cholesterol lowering medication, including paricalcitol (commercially available as Altocor®), pitavastatin (commercially available as Livalo®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pavastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NR®), and acetaminophen, codeine phosphate (commercially available as Tylenol with Codeine®); medication for the treatment of diabetes, including pioglitazone hydrochloride, metformin hydrochloride (commercially available as ACTOplus Met®), bromocriptine mesylate (commercially available as Cycloset®), liraglutide (commercially available as Victoza®), saxagliptin (commercially available as Onglyza®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia®), exenatide (commercially available as Byetta®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance®), metformin hydrochloride (commercially available as Glumetza®), sitagliptin (commercially available as Januvia®), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), and tolazamide (commercially available as Tolinase®).

Other useful agents of the present invention may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec®), pantoprazole sodium (commercially available as Protonix®), metoclopramide hydrochloride (commercially available as Reglan® or Metozolv®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®). bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Agents useful herein may also include treatment for emphysema, such as tiotropium bromide (commercially available as Spiriva®); fibromyalgia medication, such as milnacipran hydrochloride (commercially available as Savella®); medication for the treatment of gout, such as colchicine (commercially available as Colcrys®), and febuxostat (commercially available as Uloric®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide (commercially available as Zonegran®), levetiracetam (commercially available as Keppra®), and phenyloin sodium (commercially available as Dilantin®).

Erectile dysfunction therapies useful herein include, but are not limited to, drugs for facilitating blood flow to the penis, and for effecting autonomic nervous activities, such as increasing parasympathetic (cholinergic) and decreasing sympathetic (adrenersic) activities. Useful agents for treatment of erectile dysfunction include, for example, those agents available as alprostadil (commercially available as Caverject®), tadalafil (commercially available as Clalis®), vardenafil (commercially available as Levitra®), apomorphine (commercially available as Uprima®), yohimbine hydrochloride (commercially available as Aphrodyne®, Yocon®), and sildenafil citrate (commercially available as Viagra®).

Agents useful herein may further include eye medications and treatment, such as dipivefrin hydrochloride (commercially available as Propine®), valganciclovir (commercially available as Valcyte®), ganciclovir ophthalmic gel (commercially available as Zirgan®); bepotastine besilate (commercially available as Bepreve®), besifloxacin (commercially available as Besivance®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); influenza medication, such as haemophilus b conjugate vaccine; tetanus toxoid conjugate (commercially available as Hiberix®); and heart treatments, including quinidine sulfate, isosorbide dinitrate/hydralazine hydrochloride (commercially available as BiDil®), digoxin (commercially available as Lanoxin®), flecamide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful agents include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enalaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), Guanabenz acetate. (commercially available as Wytensin®), Guanfacine hydrochloride (commercially available as Tenex® or Intuniv®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

The present invention may include agents useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase®), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, and Novolin®); and HPV treatment, such as Human papillomavirus vaccine (commercially available as Gardasil®) or human papillomavirus bivalent (commercially available as Cervarix®); immunosuppressants, including cyclosporine (commercially available as Gengraf®, Neoral®, Sandimmune®, and Apo-Cyclosporine®).

Agents useful in the present invention may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), synthroid (commercially available as Levothroid®, Levoxyl®, Unithroid®), testosterone (commercially available as Testopel®, Androderm®, Testoderm®, and AndroGel®); menopause medication, such as estradiol/norethindrone acetate (commercially available as Activella®), drospirenone/estradiol (commercially available as Angeliq®), estradiol/levonorgestrel (commercially available as Climara Prot), estradiol/norethindrone acetate (commercially available as CombiPatch®), estradiol (commercially available as Estrasorb®, Vagifem® and EstroGel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), tranexamic acid (commercially available as Lysteda®), and norethindrone acetate (commercially available as Aygestin®); and muscle relaxants, including cyclobenzaprine hydrochloride (commercially available as Flexeril®), tizanidine (commercially available as Zanaflex®), and hyoscyamine sulfate (commercially available as Levsin®).

Agents useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease® or Zenpep®); medication for the treatment of Parkinson's disease, such as pramipexole dihydrochloride (commercially available as Mirapex®), ropinirole hydrochloride (commercially available as Requip®), carbidopa/levodopa (commercially available as Sinemet CR®), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); multiple sclerosis medication, such as dalfampridine (commercially available as Ampyra®) and interferon beta-I b (commercially available as Extavia®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Films of the present invention may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft®), asenapine (commercially available as Saphris®), iloperidone (commercially available as Fanapt®), paroxtine hydrochloride (available as Paxil®), aripiprazole (commercially available as Abilify®), guanfacine (commercially available as Intuniv®), Amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid) (commercially available as Depakote®), dextroamphetamine sulfate (commercially available as Dexedrine®), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil®), protriptyline hydrochloride (commercially available as Vivactil®), bupropion hydrochloride (commercially available as Wellbutrin®, Wellbutrin SRC), and Wellbutrin XR®), and olanzapine (commercially available as Zyprexa®).

Agents useful herein may also include uric acid reduction treatment, including allopurinol (commercially available as Zyloprim®); seizure medications, including gabapentin (commercially available as Neurontin®), ethotoin (commercially available as Peganone®), vigabatrin (commercially available as Sabril®), and topiramate (commercially available as Topamax®); treatment for shingles, such as zoster vaccine live (commercially available as Zostavax®); skin care medications, including calcipotriene (commercially available as Dovonex®), ustekinumab (commercially available as Stelara®), televancin (commercially available as Vibativ®), isotretinoin (commercially available as Accutane®), hydrocortisone/iodoquinol (commercially available as Alcortin®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solage®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other agents useful herein may include Sleep disorder medications, including zaleplon (available as Sonata®), eszopiclone (available as Lunesta®), zolpidem tartrate (commercially available as Ambient, Ambien CR®, Edluar®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred®), desonide (commercially available as Tridesilon®), and halobetasol propionate (commercially available as Ultravate®).

Films of the present invention may further include agents useful for thyroid disease treatment, such as hormones TC and TD (commercially available as Armour Thyroid®); potassium deficiency treatment, including potassium chloride (commercially available as Micro-K®); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

Wasted constituent in the manufacturing process results in direct loss of profitability and efficiency, particularly when the constituent wasted includes one or more actives, which may be expensive. As such, it is desirable to limit the amount of wasted product in the manufacturing process in order to conserve costs and promote efficiency in production. One way to minimize cost is, of course, to limit the amount of wasted film and film-forming compositions. Thus, the present invention is directed to methods of forming film products that reduce the amount of waste associated with traditional film forming methods. In a preferred embodiment, at least one individual film product is directly formed in the desired size, which reduces or altogether eliminates the need for cutting and sizing the film product. In another embodiment, the individual film product is formed directly onto the surface of a package, which may then be sealed and distributed to a user. In both of these embodiments, since there is no sizing of the film product required, there is little to no wasted material. As will be explained in further detail below, however, it is critical that the film product be capable of being adhered to the package surface during the manufacturing stage, but be capable of being easily removed from the package by the user at a later time.

Forming the Film

The dosage form of the present invention may be a film, as defined above. A flowable film-forming matrix is first prepared, and desirably the matrix is substantially uniform in content. A film-forming matrix may be prepared in any desired method including any desired components, including those methods and components described in U.S. Pat. Nos. 7,425,292, 7,357,891 and 7,666,337, the contents of which have been incorporated herein into this application. For example, a film-forming matrix may include one or more polymers, one or more solvents, one or more active components, and any other desired components, such as sweeteners, flavors, fillers, and the like. Uniformity of content of the matrix is desirably maintained as the flowable matrix is formed into a film and dried.

Typical polymers that may be used in the formation of the present films include those described in U.S. Pat. No. 7,666, 337. The polymer may be water soluble, water swellable, water insoluble, or a combination of one or more either water soluble, water swellable or water insoluble polymers. As used herein the phrase "water soluble polymer" and variants thereof refer to a polymer that is at least partially soluble in water, and desirably fully or predominantly soluble in water, or absorbs water. The polymer may include cellulose or a cellulose derivative. Specific examples of useful water soluble polymers include, but are not limited to, polyethylene oxide (PEO), pullulan, hydroxypropylmethyl cellulose (HPMC), hydroxyethyl cellulose (HPC), hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly (lactic acid) (PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100L, believed to be 100% lactide having a melting point within the range of 338°-347° F. (170°-175° C.); lactide/glycolide 100L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

The Biodel materials represent a family of various polyanhydrides which differ chemically.

Although a variety of different polymers may be used, it is desired to select polymers to provide a desired viscosity of the mixture prior to drying. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active in the film forming matrix, which may be in the form of an emulsion, a colloid, a dispersion, or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Additionally, polyethylene oxide (PEO), when used alone or in combination with a hydrophilic cellulosic polymer, achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

In one embodiment of the present invention, PEO desirably ranges from about 20% to 100% by weight in the polymer component. In some embodiments, the amount of PEO desirably ranges from about 1 mg to about 200 mg. The hydrophilic cellulosic polymer ranges from about 0% to about 80% by weight, or in a ratio of up to about 4:1 with the PEO, and desirably in a ratio of about 1:1. In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component. For instance, certain film properties, such as fast dissolution rates and high tear resistance, may be attained by combining small amounts of high molecular weight PEOs with larger amounts of lower molecular weight PEOs.

The film products are generally formed by combining a properly selected polymer and solvent, as well as any agent or filler as desired to form a film forming matrix, desirably a flowable matrix. In some embodiments, the solvent content of the combination may be at least about 30% by weight of the total combination, but may be lower for a film forming matrix having a higher solids percentage. The matrix formed by this combination is formed into a wet film product and then dried to provide a film product. The film product is desirably a self-supporting film product, which may be formed by a rapid and controlled drying process to maintain the uniformity of the film, more specifically, a non-self-aggregating uniform heterogeneity. The resulting film will desirably contain about 10% by weight or less solvent, more desirably about 8% by weight or less solvent, even more desirably about 6% by weight or less solvent and most desirably about 2% or less solvent. The solvent may be water, a polar organic solvent including, but not limited to, ethanol, isopropanol, acetone, methylene chloride, or any combination thereof.

Controlled Release Films

The term "controlled release" is intended to mean the release of the components at a pre-selected or desired rate. For example, in embodiments where the film includes nanoparticles within the body of the film, it may be desirable to control its release from the film. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed releases of the agent are also contemplated.

Dissolvable films generally fall into three main classes: fast dissolving, moderate dissolving and slow dissolving. Films of the present invention may be dissolvable in the presence of liquid, such as in the oral cavity of the user or when mixed with a liquid, such as water. Fast dissolving films generally dissolve in about 1 second to about 30 seconds. Moderate dissolving films generally dissolve in about 1 to about 30 minutes, and slow dissolving films generally dissolve in more than 30 minutes, e.g., up to about 60 minutes or more. Fast dissolving films may consist of low molecular weight hydrophilic polymers (i.e., polymers having a molecular weight between about 1,000 to 200,000). In contrast, slow dissolving films generally have high molecular weight polymers (i.e., having a molecular weight in the millions).

Moderate dissolving films tend to fall in between the fast and slow dissolving films. Moderate dissolving films dissolve rather quickly, and can also have a good level of mucoadhesion. Moderate films are also flexible, quickly wettable, and are typically non-irritating to the user. For oral-dissolving films, moderate dissolving films are preferred, since such films provide a quick enough dissolution rate (between about 1 minute and about 30 minutes), while providing an acceptable mucoadhesion level such that the film is not easily removable once it is placed in the oral cavity of the user.

The polymers that are chosen for the films of the present invention may also be chosen to allow for controlled disintegration of the components. This may be achieved by providing a substantially water insoluble film that will allow active components to be released from the film over time. This may be accomplished by incorporating a variety of different soluble or insoluble polymers and may also include biodegradable polymers in combination. Alternatively, coated controlled release agent particles may be incorporated into a readily soluble film matrix to achieve the controlled release property of the active. The polymers used for preparing the film matrix may be water-soluble, partially water-soluble, water swellable or a combination of polymers which may be soluble, partially soluble and/or swellable.

In some embodiments a combination of a sustained release (or slow dissolving) film layer may be combined with a layer of fast dissolving film. The active or active-containing component, may be in one layer or may be in both layers. In one embodiment, the active or active-containing component is in a fast dissolving (or fast release) film layer and a slower, sustained release layer may be laminated or otherwise attached thereto. The fast release layer may be intended to be placed against a mucosal or organ tissue surface and the slow, sustained release layer may be an exclusive layer which covers and protects the fast dissolving layer, as well as adhering the total film unit to the mucosal or body site, e.g., as in a buccal application.

The convenience of administering a single dose of a medication which releases components in a controlled fashion over an extended period of time (i.e., an extended period of time may include a time period that is more than one minute, more than 5 minutes, more than 10 minutes, or more than 30 minutes), as opposed to the administration of a number of single doses at regular intervals has long been recognized in the pharmaceutical arts. The advantage to the patient and clinician in having consistent and uniform levels of medication delivered to the body over an extended period of time are likewise recognized.

Optional Components

A variety of other components and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; and thermo-setting gels such as pectin, carageenan, and gelatin, which help in maintaining the dispersion of components.

The variety of additives that can be incorporated into the inventive compositions may provide a variety of different functions. Examples of classes of additives include lubricants, buffering agents, stabilizers, blowing agents, pigments, coloring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water soluble polysaccharides such as alginates, carrageenans, guar gum, agar-agar, xanthan gum, gellan gum, gum arabic and related gums (gum ghatti, gum karaya, gum tragancanth), pectin, water soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be glidants and opacifiers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the texture of the film composition such as animal or vegetable fats, desirably in their hydrogenated form, especially those which are solid at room temperature. These fats desirably have a melting point of 50° C. or higher. Preferred are triglycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about five percent (5%) and preferably within the range of about 0.5% to about two percent (2%) by weight of the total composition.

It is further useful to add silicon dioxide, calcium silicate, or titanium dioxide in a concentration of about 0.02% to about 1% by weight of the total composition. These compounds act as opacifiers and flow agents.

These additives are to be used in amounts sufficient to achieve their intended purpose. Generally, the combination of certain of these additives will alter the overall release profile of the active ingredient and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier, which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

As additional modifiers that enhance the procedure and product of the present invention are identified, Applicants intend to include all such additional modifiers within the scope of the invention claimed herein.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Films of the present invention, particularly films useful for oral ingestion by a user, may further include one or more taste-enhancing agents, such as flavors and/or sweeteners, including sugar and sugar alcohols. Suitable flavors and sweeteners include those set forth in U.S. Pat. No. 7,425,292.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

The various embodiments of the invention may include penetration and permeation enhancers. Among such useful enhancers are included medium chain mono- and diacylglycerol fatty acid derivative, such as glycerol laurate, and mixtures thereof; synthetic and natural surfactants and mixtures thereof; medium chain fatty acids and salts and esters thereof, including mono-, di- and triglycerides such as sodium caprylate and sodium caprate and mixtures thereof; bile salts; chelating agents, such as EDTA; detergents; cylodextrins, enamine derivatives, phospholipids, lecithins, cetomacrogels, sodium salicylate, sodium-5-methoxysalicyclic acid; glycerol and polyethylene glycol estess such as those sold under the name Labrasol; zonula occludens toxin; and alkyl glycosides. Additionally, combinations of penetration and permeation enhancers from different classes are also useful.

Additional permeation enhancers include, polysorbate 80, phosphatidylcholine, n-methylpiperazine, sodium salicylate, melittin, and palmitoyl carnitine chloride (pcc). 23-lauryl ether, aprotinin, azone, benzalkonium chloride, cetylpyridinium chloride, cetyltrimethylammonium bromide, cyclodextrin, dextran sulfate, lauric acid, lauric acid/propylene glycol, lysophosphatidylcholine, menthol, methoxysalicylate, methyloleate, oleic acid, phosphatidylcholine, polyoxyethylene, sodium edta, sodium glycocholate, sodium taurocholate, sodium lauryl sulfate, sodium salicylate, sodium glycodeoxycholate, sodium taurodeoxycholate, sulfoxides, and combinations thereof.

Additional permeation and/or penetration enhancers include dimethylsulfoxide, decylmethylsulfoxide, alkysulfoxides: alkanols, such as ethanol, propanol, butanol, pentanol, hexanol, octanolnonanol, decanol, 2-butanol, 2-pentanol, benzyl alcohol; fatty alcohol acids and their corresponding alcohols, such as caprylic, decyl, lauryl, 2-lauryl, myristly, cetyl, stearyl oleyl, linoleyl, linolenyll alcohol; linear carboxylic acids such as: valeric, heptanoic, pelagonic, caproic, capric, lauric, Myristic, stearic, oleic, caprylic; Branched carboxylic acids: such as isovaleric, neopentanoic, neoheptanoic, neononanoic, trimethyl hexanoic, neodecanoic, isostearic; fatty acid esters, such as aliphatic-isopropyl n-butyrate, isopropyl n-hexanoate, isopropyl n-decanoate, isopropyl myristate, isopropyl palmitate, octyldodecyl myristate; alkyl esters such as ethyl acetate, butyl acetate, methyl acetate, methylvalerate, methylpropionate, diethyl sebacate, ethyl oleate; propylene glycol, polyethylene glycol, ethylene glycol, diethylene glycol, triethylene glycol, dipropylene glycol, glycerol, propanediol, butanediol, pentanediol, hexanetriol, urea, dimethylacetamide, diethyltoluamide, dimethylformamide, dimethyloctamide, dimethyldecamide; biodegradable cyclic urea, such as 1-alkyl-4-imidazolin-2-one; pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2pyrrolidone, 1-methyl1-4-methoxycarbonyl-2-pyrrolidone, 1-hexyl-4-methoxycarbonyl-2 pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkylpyrrolidone; biodegradable pyrrolidone derivatives such as the fatty acid esters of N-(2-hydroxyethyl)-2-pyrrolidone; cyclic amides such as 1-dodecylazacycloheptane-2-one (Azone), 1-geranylazacycloheptan-2-one, 1 farnesylazacycloheptan-2-one, 1-teranylgeranylazacycloheptan-2-one, 1-(3,7-dimethyloctyl)azacycloheptan-2-one, 1-(3,7,11-trimethyldodecyl)azacyclohaptan-2-one, 1-geranylazacyclohexane-2-one, 1-geranylazacyclopentan-2.5-dione, 1-farnesylazacyclopentan-2-one; hexamethylenelauramide and its derivatives; diethanolamine, triethanolamine; anionic surfactants such as sodium laurate, sodium lauryl sulphate; cationic surfactants such as cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride; nonionic surfactants including block copolymers of polyoxyethylene/polyoxypropylene/polyoxyethylene (such as those sold under the tradenames Poloxamer 231, 182, and 184), polyoxyethylene dodecyl ethers (sold under the tradename Brij 30), polyoxyethylene monooleyl ethers (sold under the tradenames Brij 93, 96 and 99), sorbitan fatty acid esters such as those sold under the tradenames Span (20, 40, 60, 80, 85), sorbitan monosterates such as those sold under the tradenames Tween (20, 40, 60, 80), polyethylene glycol monosterates such as those sold under the tradenames Myrj (45, 51, 52), and propylene glycol dicaprylate/dicaprate sold under the tradenames Miglyol 840 and others; bile salts such as sodium cholate, sodium salts of taurocholic, glycholic and desoxycholic acids; lecithin; hydrocarbons such as D-Limonene, a-pinene, B-carene; alcohols such as a-terpineol, terpinen-4-ol, carvol; ketones such as carvone, pulegonee, piperitone, menthone; oxides such as cyclohexene ocide, limonene oxide, a-pinene oxice, cyclopentene oxide, 1,8-cineole; oils such as Ylang ylang, anise, chenopodium, eucalyptus; N-heptane, N-octane, N-nonane, N-decane, N-undecane, N-dodecane, N-tridecane, N-tetradecane, N-hexadecane; salicylic acid and salicylates (including their methyl, ethyl, and propyl glycol derivatives); citric and succinic acid.

As previously stated, combinations of penetration and permeation enhancers from different classes are also useful. Combinations of alcohols and other permeation enhancers are useful. For example ethanol and isopropanol may be used as a combination. These alcohols may further be used in combination with other permeation and/or penetration enhancers described herein as mixtures or solutions. For example, non-limiting useful combinations include ethanol in combination with one or more components selected from cyclic monoterpenes, propylene glycol dicaprylate/decaprate (sold under the tradename Miglyol 840), Ethyl acetate, oleic acid, 1-menthol, urea, glycerides, triesters of glycerin and aliphatic acids such as tricaprylin (sold under the tradename Panasate 800), propylene glycol, urea, water: and isopropanol in combination with components such as polyoxyethylene sorbitan monooleate (sold under the tradename Tween 80), isopropyl myristate, isopropyl myristate, lauric acid, lauryl alcohol and Na lauryl sulphate.

The permeation enhancers promote and/or enhance the absorption of the active. Enzyme inhibitors may also be employed to protect sensitive biological active agents from being destroyed prior to absorption. The permeation enhancers may be used in various effective amounts in the film depending upon the specific formulation and active. Generally, permeation enhancers may be present in amounts of about 15% to about 25%, used more desirably in amounts of 0.01% to about 15%, by weight of the total film composition.

Forming the Film

In one particular method of forming a film, a wet film-forming matrix is deposited directly onto the surface of a substrate. Any desired substrate may be used, including, for example, mylar, paper, plastic, metal, foil, and combinations thereof. The substrate may be laminated if desired. Further, the substrate may be chemically treated prior to depositing the wet film matrix thereon. Desirably, the substrate is substantially flat, but is flexible to allow for rolling, such as for storage or for packaging of the formed film products. In a preferred embodiment, the substrate is made of a material suitable for packaging and ultimate distribution of the film product. Thus, the substrate should be commercially acceptable to house and store a film product, and should comply with any federal regulations governing packaging of the product housed therein. In some embodiments, the substrate may include at least one layer of a pre-formed sheet or film thereon, where the wet film products are deposited directly onto the pre-formed sheet or film.

The substrate may have any length and width desired, depending on the size of the apparatus used to process the film. The length of the substrate is not critical, since the substrate may generally be fed into the film-forming apparatus on a continuous basis and sized by the user accordingly. The entire length of the substrate may be at least 50 meters, at least 100 meters, at least 200 meters, or any desired length. The width of the substrate is sized so that it may be fed into the apparatus used, and may vary as desired. The width of the substrate typically determines the width of the film product that can be prepared on that substrate. For example, a plurality of individual wet film forming products may be deposited on the substrate, arranged in a substantially side-by-side manner. The number of rows of product multiplied by the width of the final package dictates the desired width of the substrate (i.e., the total of the widths of each film forming product package is approximately the minimum width for the substrate). It is typical then that the number of products across the web may help determine the optimum width of the substrate.

The width of the individual film products may be relatively small, for example, between about 2 to about 30 mm in width. Alternatively, the width of the individual film products may be larger, such as above 30 mm in width. Any desired width may be used, and the overall width of the substrate may be adjusted as necessary. It should be contemplated that the width and length of a dried film product may, in some instances, be smaller than the width and length of the wet film product from which it is formed, due to the evaporation of solvents. If desired, the wet film forming products may be substantially square or rectangular in shape, but any other shapes may be used.

There may be deposited onto the surface of the substrate any number of individual wet film forming products, generally deposited in a series of columns. In some embodiments, there may be deposited between about 2 to about 30 columns of individual wet film forming products on a substrate, the wet film forming products arranged in a substantially side-by-side fashion. Any number of columns of individual wet film forming products may be deposited, and may be adjusted as necessary to conform to the width of the individual products and/or the width of the substrate.

It is particularly preferred that there be a gap or space between adjacent wet film forming products (and ultimately the dried film products) both along the length and width, to allow for sealing, packaging, cutting and ultimately distribution. FIG. 1 depicts one arrangement of a plurality of wet film forming products 10 deposited onto a top surface 25 of a substrate 20. As can be seen in this Figure, each wet film forming product 10 is deposited in a substantially side-by-side fashion, with a space or gap 30 between adjacent wet film forming products 10 arranged to their side. In addition, the wet film forming products 10 are deposited with a space or gap 40 between adjacent wet film forming products 10 arranged along the length of the substrate 20. The spaces 30, 40 will ultimately aid in packaging the final film products. Thus, it is desirable that the wet film forming products 10 be deposited in a series of rows and columns, separated by spaces 30, 40.

In use, at least one individual wet film forming product 10 is deposited onto the top surface 25 of the substrate 20. The individual wet film forming products 10 may be deposited via any desired means. In a preferred embodiment, the wet film forming products 10 are deposited onto the substrate 20 via extrusion, however, the wet film forming products 10 may be deposited onto the substrate 20 via any means desired, including coating, casting, spraying, or other means. In one particularly useful embodiment, the wet film forming products 10 are coated directly onto the surface 25 of the substrate 20. The wet film forming products 10 may be coated onto the surface of a pre-formed film, thus forming a multi-layered film product. The wet film forming products 10 are deposited in such a fashion that each individual wet film forming product 10 includes substantially the same amount of active composition(s), has substantially the same weight and has substantially the same dimensions, although slight variations in the weight and/or dimensions is to be expected. For example, each wet film forming product 10 may vary by about 10% or less in content, weight, and/or dimensions as compared to each other.

The individual wet film forming products 10 may be deposited onto the substrate 20 by any desired means, but are desirably deposited by one of three methods, including off-set printing (gravure), direct printing (gravure) and start-and-stop slot die coating (also referred to as patch coating). For off-set printing, the liquid film forming matrix is transferred to an etched design roller, where the excess matrix is removed via a doctor blade, and the matrix is transferred to a print roller. The print roller transfers the desired amount of matrix to the surface 25 of the substrate 20, thus forming an individual wet film forming product 10. For direct gravure printing, the matrix is desirably transferred to an etched design roller, where the excess is doctored off, but the matrix is then directly transferred to the top surface 25 of the substrate 20. Slot die coating is particularly preferred, and start-and-stop slot die coating is specifically preferred. In this method, a metering pump is used to move a coating die against the surface 25 of the substrate 20 while dispensing a predetermined amount of matrix, and then moving the coating die away from the top surface 25 of the substrate 20 while the matrix is not dispensed. This process is repeated as often as desired to prepare a plurality of wet film forming products 10. Further, the speed at which the coating die is moved, and the rate at which the matrix is dispensed by the metering pump may be controlled to dispense a particular amount of matrix. The distance between adjacent film forming products 10 may be controlled in both the width direction as well as the length direction (i.e., the gaps 30 and 40 may be controlled). Through this technique of controlled coating onto the top surface 25 of the substrate 20, the individual wet film forming product 10 may be coated and dried in the exact location that it will exist in the final package. The present methods completely remove the requirement of transferring a dried film product to a separate substrate, thus eliminating the potential for damage to the product during the transfer process. In addition, the present methods remove the loss of product as waste, which may be incurred when a wide continuous roll is edge trimmed and then cut into smaller rolls for packaging. These smaller rolls may also be edge trimmed, which leads to further losses. The present methods also eliminate a process step of slitting film, which results in about 5-13% wasted materials.

The wet film forming products 10 are generally deposited in discrete amounts, such that the deposited wet film forming products 10 each have a width and length that is capable of being dried to form an individual film product having the desired width and length. Each wet film forming products 10 desirably contains an active component in a known amount, such that each resulting dried film product will have a known active content.

When the wet film forming products 10 are deposited onto the top surface 25 of the substrate 20, it is important that there be a sufficient surface tension of the wet film forming products 10. If the surface tension is too low, the deposited wet film forming products 10 may spread out or bleed out on the top surface 25 of the substrate 20. The surface tension of the wet film forming products 10 should also be high enough to withstand any air flow present during the drying process, thus reducing the likelihood that dimensional uniformity would be compromised. When the liquid film forming product 10 is disposed on the substrate 20, the adhesive forces between the liquid and solid generally cause the liquid to spread over the solid. Cohesive forces of the liquid cause the liquid to ball up. Given this natural tendency, the force of adhesion between the liquid and solid is desirably greater than the forces of cohesion. However, it is important to achieve a balance between adhesion and cohesion. In some embodiments, the contact angle should be less than 90 degrees, since contact angles greater than 90 degrees (i.e., between 90-180 degrees) indicate no or low "wetting" of the surface. In some embodiments, it may be desirable to have a contact angle as close to 90 degrees as possible, to achieve the most optimal degree of wetting, and optionally the contact angle may be between 0 and 90 degrees. As used herein, the term "contact angle" is intended to include a measure between the liquid droplet and the solid surface (substrate 20). In some embodiments, dynamic contact angles are considered. It is desired that the deposition of the film forming product 10 sufficiently "wet" the substrate 20. The wetting of the substrate 20 may be facilitated by manipulation of the surface energy of the substrate 20 such as through addition of coatings onto the substrate or by manipulation of the surface energy of the film-forming product 10, such as by the use of surfactants.

In general, any suitable polymer or polymers that provide the desired surface tension and rheology may be used. For example, the polymer(s) may be more hydrophilic in nature, or may be more lipophilic. In general, any water soluble polymer or dispersible polymer will suffice, as long as the overall liquid properties of the polymer solution allow for wetting to the substrate 20 and supply the adhesion forces required to adhere to the substrate 20 during processing, while also facilitating removal of the ultimate film by the user.

It may further be desired that the dried film products be stored for an extended period of time before packaging. In one embodiment, after drying, the storage is achieved by rolling the substrate 20 (with dried film thereon) and placing the rolled substrate 20 in storage for a determined period of time. When it is desired that the dried films be packaged, the rolled substrate 20 is unrolled, and the film products are packaged, as will be described in further detail below. It is important that the dried film be sufficiently adhered to the top surface 25 of the substrate 20 during rolling and storage, and also remain adhered during the unrolling phase. This may be facilitated by rolling the substrate and film with a release liner. The release liner may be made from any material, including polyvinyl chloride, polyester (PET), polypropylene, polystyrene, PET/polyethylene (including high-density polyethylene, low-density polyethylene, and linear low-density polyethylene). Paper release liners may also be used, and may be made from a super-calendered kraft liner (SCK), which may be coated with either silicone or polyethylene.

However, it is important that the dried film products be capable of easy removal by the consumer from the top surface 25 of the substrate 20. This is particularly true when the substrate 20 is a material which will be used as the direct packaging of the film product. Since the film product will be provided to a user, it is important that the user be capable of removing the film product from the top surface 25 of the substrate 20 without having the film product stick to the substrate 20 and risk tearing.

The fundamental equations that govern adhesion and spreading are expressed as the Young-Dupre equations:

$$\gamma_{SV} = \gamma_{SL} + \gamma_{LV} \cos \theta \qquad \text{(equation 1)}$$

$$\omega_A = \gamma_{SV} + \gamma_{LV} - \gamma_{SL} \qquad \text{(equation 2)}$$

where $\gamma_{SV}$ is the interfacial tension between a solid and a vapor, $\gamma_{SL}$ is the interfacial tension between a solid and a liquid, $\gamma_{LV}$ is the interfacial tension between a liquid and a vapor, $\theta$ is the contact angle at the solid-liquid interface, and $\omega_A$ is the work of adhesion. The surface of the solid (the substrate or packaging material) will fully wet as both the interfacial tension between the liquid vapor interface (LV) and the contact angle goes to zero. Angles less than 90° are generally preferred, but the contact angle may be 150° or less. The force needed to pull the dried film from the substrate must be greater than the shear force from the air flow or from any other stresses encountered during the drying and packaging process. In this way, the film will remain adhered to the package until it is desired to be removed. Thus, it is desired that the force required to remove the dried film from the substrate be less than that required to deform or overcome the tensile strength of the dried adhered film.

To achieve the balance between a sufficient surface tension of the wet film forming products 10 and the ease of removing the resulting dried film product from the substrate 20, the present invention may utilize several different methods. One such method is using surface active agents that can adjust the interfacial tension of the liquid (the wet film forming products 10) and solid (the top surface 25 of the substrate 20).

Another way to provide for the proper adhesion balance is to incorporate a polymer or other excipient in the wet film forming matrix. The polymer or other excipient will be used as a crystallization component. For example, one such crystallization component (or crystallization promoter) may include a sugar alcohol, such as xylitol. The polymer or other excipient is capable of drying in the film as an amorphous structure, improving adhesion of the wet film forming products 10 and the resulting dried film to the substrate 20. However, over time, the crystallization component crystallizes, thereby making the dried film less plasticized and less adhered to the top surface 25 of the substrate 20. Thus, the dried film is easily removed from the package after a period of time. It is particularly desired that the crystallization component crystallize over a length of time suitable for storage after drying and prior to final packaging. Ideally, this time should be at least one day and as many as 30 days after drying. In some embodiments, the dried film should not release within the first 14 days after drying, allowing sufficient time for the packaging process to be completed. The film may be capable of releasing within 30 days or longer, so that the product will be available to the user after the packaging and commercialization of the product is complete. Depending, of course, on the packaging, marketing and demand for the product, the release dates may be adjusted to provide a longer or shorter time period.

Yet another way to balance the adhesion between wet film forming products 10 and resulting dried film products is to store the dried film (on the substrate 20) at a temperature below room temperature for a desired period of time. Storage of the dried film on the substrate 20 for a lower temperature decreases the adhesion of the dried film product, allowing its ease of removal from the package. The packaged dose may then be delaminated from the packaging material using any number of techniques, including vibration, movement over a mandrel, and the like. Another way to balance the adhesion is to adjust the surface properties of the substrate 20. For example, the substrate 20 may be coated with one or more coatings, including, hydrophilic coatings and/or hydrophobic coatings, or it may undergo static treatment, Corona treatment, electron beam treatment, and combinations thereof.

In some embodiments, the present invention may incorporate various combinations of the above methods. For example, the wet film forming matrix may include at least one crystallization component and the dried film may be stored at a temperature below room temperature. Alternatively, the wet film forming matrix may include a surface active agent and the dried film may be stored at a cool temperature. Further, the present invention may include all of the above methods.

One benefit that the present invention provides is that the films of the present invention may allow for higher loading of active, while at the same time allowing for disintegration in the mouth in the desired time frame. Traditional film manufacturing requires that the wet film deposited and the resultant dried film have enough integrity to withstand all of the processing steps. To get this integrity, the ideal polymer concentration and molecular weight is sometimes compromised, thus resulting in slower disintegration in the mouth or other body cavity. With the present invention, the dried film products only require enough integrity to stay intact while being removed from the pouch and placed into the mouth or other body cavity. This is because the additional processing steps of cutting, sizing, and transferring have been reduced or eliminated.

Drying the Film

As explained above, once the wet film forming product(s) 10 have been deposited onto the surface of the substrate 20, the products 10 are dried to provide dried film products 50. The films of the present invention may be dried in any desired manner, including through the use of conventional drying ovens, or in those methods disclosed in U.S. Pat. Nos. 7,425, 292 and 7,357,891, which are incorporated herein by reference in their entireties.

Thermal mixing helps to maintain a lower overall temperature inside the film. Although the film surfaces may be exposed to a temperature above that at which the active component degrades, the film interior may not reach this temperature. Due to this temperature differential, the active does not degrade. For instance, the films of the present invention desirably are dried for ten (10) minutes or less. Drying the films at 80° C. for ten (10) minutes produces a temperature differential between the atmosphere and the film matrix of about 5° C. This means that after ten (10) minutes of drying, the temperature of the inside of the film is 5° C. less than the outside exposure temperature. In many cases, however, drying times of less than ten (10) minutes are sufficient, such as four (4) to six (6) minutes. Drying for four (4) minutes may be accompanied by a temperature differential of about 30° C., and drying for six (6) minutes may be accompanied by a differential of about 25° C. Due to such large temperature differentials, the films may be dried at efficient, high air temperatures without causing heat sensitive actives to degrade, and without causing the matrix to reach a temperature where the active becomes substantially unstable, substantially degrades or becomes less active.

Once a sufficient amount of the volatile liquid has evaporated, thermal mixing has produced uniform heat diffusion throughout the film. The components desirably are locked into a uniform distribution throughout the film, and the final shape of the film is established. It may be desired to form a visco-elastic solid rapidly, for example within the first ten (10) minutes or less, desirably within the first six (6) minutes or less, and most desirably within the first 0.5 minutes to four (4) minutes. Although minor amounts of liquid carrier, i.e., water, may remain subsequent to formation of the visco-elastic film, the film may be dried further without affecting the desired heterogeneity of the film, if desired. Further drying forms the final film, by desirably removing solvent from the visco-elastic solid such that less than ten percent (10%) of solvent remains, and more desirably less than eight percent (8%) of solvent remains, and most desirably less than six percent (6%) of the solvent remains in the final film.

While the air temperatures for drying may be about 50° C. to about 160° C., the temperatures of the film matrix are generally less than the boiling temperature of the solvent in the matrix. The temperature of the film forming matrix during drying is desirably about 100° C. or less, desirably about 90° C. or less, and most desirably about 80° C. or less. The air temperature may be substantially greater than the film matrix temperature provided that no substantial deleterious effects are imparted on the film matrix or the active or active-containing component or particles. It may be desired to dry the film such that the temperature within the film is less than the boiling point of any solvent or solvents that are within the film forming matrix. Further, it is desirable that the temperature within the film forming matrix is maintained below the degradation temperature of any actives contained within the film. It is noted, however, that the temperature outside of the film may be above the temperature within the film, and in some instances may be substantially higher than the temperature within the film.

The film products are generally formed by combining a properly selected polymer and polar solvent, as well as any agent or filler as desired. Desirably, the solvent content of the combination is at least about 30% by weight of the total combination. The material formed by this combination is formed into a film, desirably by roll coating, and then dried, desirably by a rapid and controlled drying process to maintain the uniformity of the film, more specifically, a non-self-aggregating uniform heterogeneity. The resulting film will desirably contain about ten percent (10%) by weight or less solvent, more desirably about eight percent (8%) by weight or less solvent, even more desirably about six percent (6%) by weight or less solvent and most desirably about two percent (2%) or less solvent. The solvent may be water, a polar organic solvent including, but not limited to, ethanol, isopropanol, acetone, or any combination thereof.

Furthermore, actives or active-containing particles or particulates may be added to the film-forming composition or material after the composition or material is cast into a film. For example, such actives may be added to the film forming matrix prior to the drying of the film, or alternatively may be added to the surface of the dried film. Active-containing particles may be controllably metered to the film and disposed onto the film through a suitable technique, such as through the use of a doctor blade, which is a device which marginally or softly touches the surface of the film and controllably disposes the particles onto the film surface. Other suitable, but non-limiting, techniques include the use of an additional roller to place the active-containing particles on the film surface, spraying or depositing the active onto the film surface, adding the active by either simple (applied to dry backing film) or dual slot die extrusion (backing film and particles formed simultaneously) and the like. The actives or active-containing particles may be placed on either or both of the opposed film surfaces, i.e., the top and/or bottom film surfaces by deposition techniques. Deposition techniques would include the ability to accurately meter the amount of active-containing particles onto the surface of the film. In some embodiments, the active-containing particles may be dispersed in a fluid medium and the dispersion deposited on the film, such as in a coating layer. Desirably, the particles are securably disposed onto the film, such as being embedded into the film. Moreover, such particles are desirably not fully encased or fully embedded into the film, but remain exposed to the surface of the film, such as in the case where the particles are partially embedded or partially encased.

The uniformity of the present invention is determined by the presence of no more than a ten percent (10%) by weight of the pharmaceutical, biological, bioeffecting, active-containing component and/or cosmetic variance throughout the matrix. Desirably, the variance is less than six percent (6%) by weight, less than two percent (2%) by weight, less than one percent (1%) by weight, or less than 0.5% by weight. In embodiments where a plurality of individual dosage units of substantially the same size are formed, it is desirable that the active content of individual dosage units has a variance of about 10% or less. Further, the contents of individual film products (i.e., products having a substantially similar size, such as the size of a dosage) formed by the present invention should desirably vary by no more than 10% by weight with respect to any other individual film product, and desirably the variance is less than 6%, less than 2%, less than 1% or less than 0.5% by weight with respect to other individual film products formed by the invention. It is to be understood that the mean of the data set is the set dosage for the product (i.e., the dosage being 10 mg, 20 mg, and the like).

The films may initially have a thickness of about 500 μm to about 1,500 μm, or about 20 mils to about 60 mils, and when dried have a thickness from about 3 μm to about 250 μm, or about 0.1 mils to about 10 mils. In some embodiments, the film product has a thickness of greater than 0.1 mils. In some other embodiments, the film product has a thickness of about 10 mils or fewer. In some further embodiments, the film product has a thickness of about 0.5 mils to about 5 mils. Desirably, the dried films will have a thickness of about 2 mils to about 8 mils, and more desirably, from about 3 mils to about 6 mils.

Sealing the Film

Once the individual film products are dried, they may be stored for any time period, as described above. Alternatively, the dried films may be packaged soon after drying is complete. Once the dried film products are sufficiently dried and are ready to be packaged, a sealing layer may be applied to the top of the substrate. The sealing layer may be any desired material, including, for example, mylar, paper, plastic, metal, foil, and combinations thereof. The sealing layer may be laminated if desired. Further, the sealing layer may be chemically treated prior to sealing. In a preferred embodiment, the sealing layer is made of a material suitable for packaging and ultimate distribution of the film product. Thus, the sealing layer should be commercially acceptable to house and store a film product.

The sealing layer and the substrate may be made from the same material or they may be different. Desirably, the sealing layer and the substrate are made from materials that may be adhered to each other, such as through methods such as heat laminating, chemical laminating, radiation, ultrasonic welding, compression, adhesive bonding (including hot melt adhesives, pressure sensitive adhesives, and the like), and combinations thereof. After attachment of the sealing layer to the substrate, with the dried film housed therebetween, the film desirably is packaged in a safe and commercially acceptable manner. It is particularly preferred that the resulting package (formed by the sealing layer and substrate) act as a barrier to moisture, thereby protecting the film housed therein.

Figure 2A:
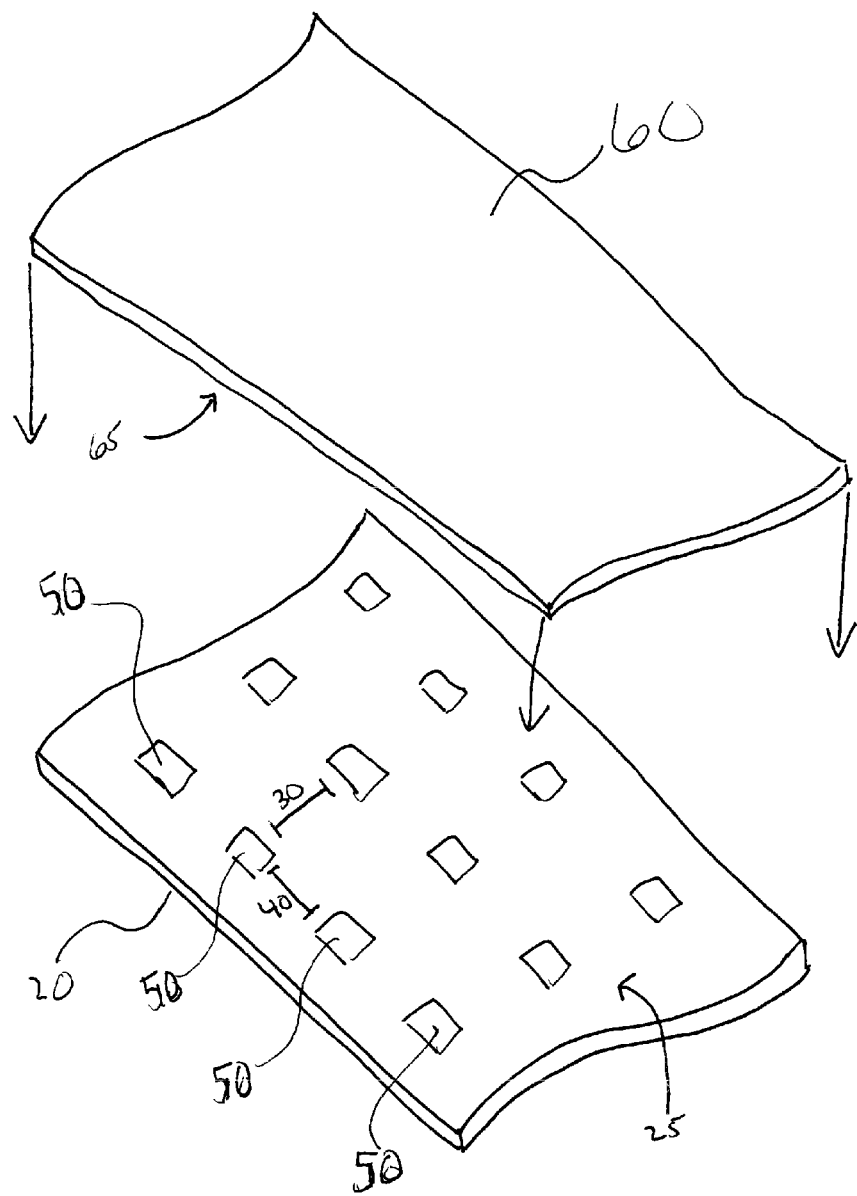
FIGS. 2A-2B depict a plurality of individual dried film products on the surface of a substrate with a sealing layer deposited thereon.
Figure 2B:
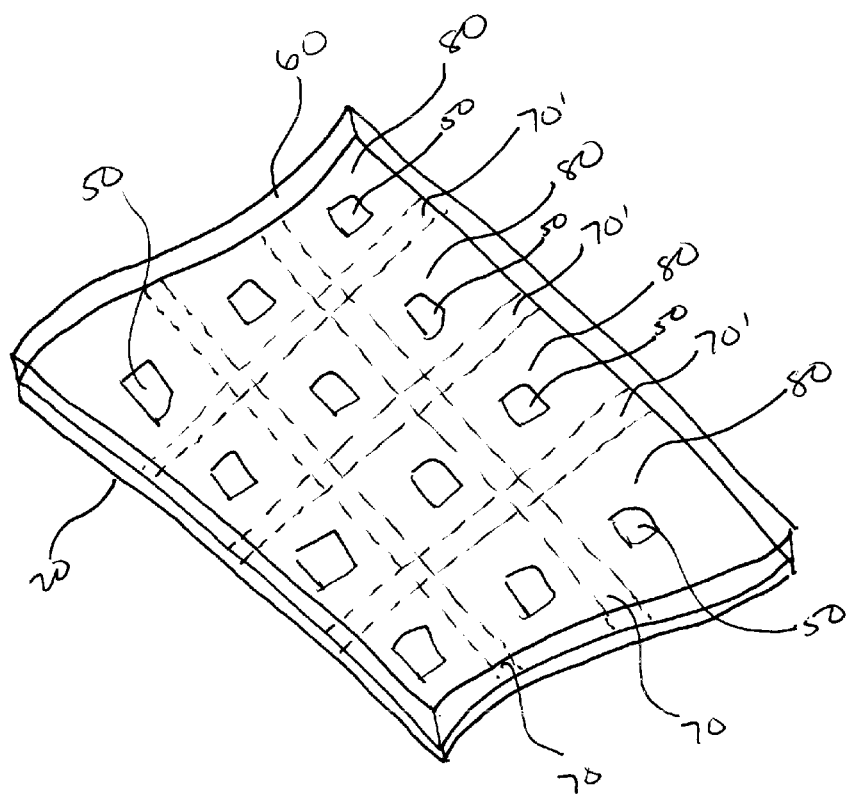

As depicted in FIGS. 2A-2B, one embodiment of the present invention is depicted. In this embodiment, the substrate 20 is covered with a second layer, forming a seal. In this embodiment, the substrate 20 includes a plurality of dried film products 50 thereon. As explained above, there is desirably a gap 30 between adjacent film products 50 along the width of the substrate 20, and desirably a gap 40 between adjacent film products 50 along the length of the substrate 20. After drying, the plurality of dried film products 50 are maintained on the top surface 25 of substrate 20, and a sealing layer 60 is provided, the sealing layer having a bottom side 65. As explained above, the dried film products 50 desirably have a sufficient adherence to the top surface 25 of the substrate 20. When the products are to be packaged, the bottom side 65 of the sealing layer 60 is placed on the top surface 25 of the substrate 20, such that at least one of the individual film products 50 is sandwiched between the substrate 20 and the sealing layer 60. For ease of reference and to aid in viewing the sealing, the sealing layer 60 in FIGS. 2A-2B is shown as a transparent layer, but it will be understood that sealing layer 60 may be opaque or translucent, and generally may have any desired coloring. For example, it may be desired that the sealing layer 60 is an opaque, laminated film layer. There may be one or more indicia or markings on the top side of the sealing layer 60, which may, for example, identify the contents of the package.

As can be seen in FIG. 2A, the sealing layer 60 is provided such that it is substantially aligned with the top surface 25 of the substrate 20. As can be seen in FIG. 2B, after the bottom side 65 of the sealing layer 60 has been placed onto the top surface 25 of the substrate 20, the sealing layer 60 is in face-to-face contact with at least a portion of the substrate 20. Desirably, the bottom side 65 of the sealing layer 60 is in direct and contiguous contact with the top surface 25 of the substrate 20 in the open areas (designated in FIG. 2A as gaps 30 and 40). The sealing layer 60 and the substrate 20 are desirably adherable to each other in desired locations. The sealing layer 60 may be adhered to the substrate 20 at adhering locations 70, 70' between the film products 50. The adhering of the sealing layer 60 to the substrate 20 thus is useful to create a plurality of individual compartments 80. Each individual film product 50 is housed within a compartment 80 defined by the adhering locations 70, 70'. It is particularly preferred that the adhering locations 70, 70' be spaced sufficiently away from the individual film products 50, so that one entire individual film product 50 is housed within one individual compartment 80. Thus, after adhering, there is a plurality of individually sealed film products 50, sandwiched between a substrate 20 and sealing layer 60. It is particularly preferred that the adhering of the sealing layer 60 and the substrate 20 form a moisture-tight barrier, to protect the individual film product 50 housed in the compartment 80.

Figure 3:
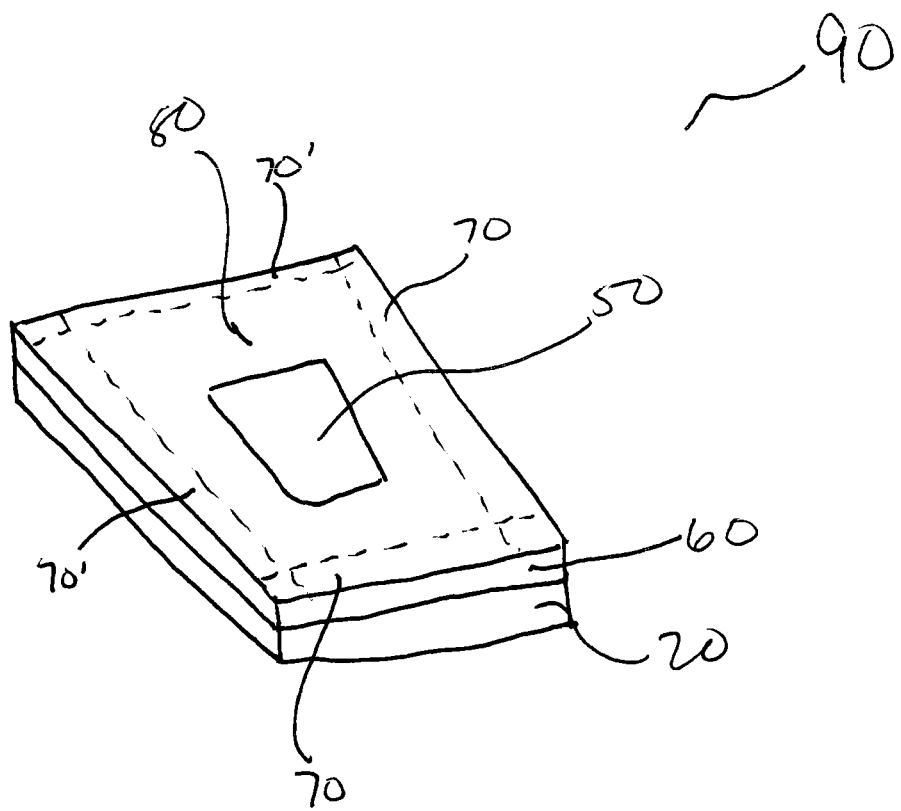
FIG. 3 depicts an individual packaged film product, which has been cut from the substrate.

Once the sealing layer 60 and the substrate 20 have been sufficiently adhered to each other, the individual compartment 80 may be cut from the substrate 20. It is, of course, desirable that the adhering locations 70, 70' be of sufficient width and length that the compartment 80 may be cut in the middle of an adhering location 70, 70', allowing adhesion to remain around the entire periphery of the film product 50. This forms a fully sealed compartment 80, protecting and housing the individual film product 50. If desired, there may be perforations or weakened areas in the adhering locations 70, 70', to allow for easier separation of the individual compartments 80. FIG. 3 depicts an individual cut film package 90, which includes substrate 20 and sealing layer 60 adhered to each other at adhering locations 70, 70', forming a compartment 80 in which the individual film product 50 is contained. Again, for ease of viewing the package, the sealing layer 60 has been depicted as a transparent layer, but may be any color or darkness desired. The compartment 80 may include a gas, such as air, in addition to the individual film product 50, or it may include the individual film product 50 in a vacuum. It is particularly preferred that the substrate 20 and sealing layer 60 be made of a material that is moisture impermeable and that is non-reactive to the film product 50. For example, the substrate 20 and/or the sealing layer 60 may be made from a laminated material. When adhered to each other, the substrate 20 and sealing layer 60 desirably form a moisture-impermeable seal, protecting the film product 50.

Uses of Films

The films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of nanoparticles to skin and other body surfaces, including those with mucous membranes and organ tissue (as defined herein).

The films may be used to administer actives through oral, or any other administration desired. Administration may be accomplished by preparing the film as described above, introducing the film to a mucosal or tissue surface of a mammal, and wetting the film if necessary, for example. If desired, this film may be prepared and adhered to a second or support layer from which it is removed prior to use, i.e. application to the skin. An adhesive may be used to attach the film to the support or backing material, which may be any of those known in the art, and is preferably not water soluble. If an adhesive is used, it will desirably be an adhesive that does not alter the properties of the active. Mucoadhesive compositions are also useful. The film compositions in many cases serve as mucoadhesives themselves.

The films of the present invention take advantage of the films' tendency to dissolve quickly when wetted, i.e., through contact with a wetting agent such as water or saliva. The films, including any actives contained therein, may be introduced to a liquid by preparing a film in accordance with the present invention, introducing it to a liquid, and allowing the film to dissolve. This may be used to prepare a liquid dosage form of the active, which may then be administered to the user.

As explained above, one embodiment provides a method of forming an individual film dosage, including the steps of: preparing a film forming matrix; providing a substrate having a top surface; depositing a pre-determined amount of the matrix onto the top surface of the substrate to form a wet film forming product; drying the wet film forming product to form a dried film product; and placing a sealing layer on the top surface of the substrate, where the sealing layer effectively seals the dried film product between the sealing layer and the substrate.

Another embodiment of the present invention provides a method of forming an individual film dosage, including the steps of: preparing a film forming matrix including at least one water soluble polymer; providing a substrate having at least one top surface; depositing a pre-determined amount of the film forming matrix onto the top surface of the substrate to form a wet film forming product; drying the wet film forming product to form a dried film product; storing the dried film product for a pre-determined length of time; and placing a sealing layer on the top surface of the substrate, where the sealing layer effectively seals the dried film product between the sealing layer and the substrate.

The methods described herein may use any desired substrate or sealing material, including for example, foil, plastic, mylar, and combinations thereof. The method may use any desired depositing methods, including off-set printing, direct printing, start-and-stop slot die coating, and the like. The dried film product may be stored for any desired time before the step of placing a sealing layer on the top surface, and storage may take place at cool temperatures, if desired. In some embodiments, the wet film forming product may be deposited onto the top surface such that at least a portion of the top surface is exposed around the periphery of the deposited wet film forming product, and then the sealing layer may be adhered to the top surface of substrate at the periphery. Adhering the sealing layer to the top surface of the substrate may thus form a compartment housing the dried film product. The method may further include the step of cutting the substrate and sealing layer to provide an individual sealed product.

The present invention may be better understood through analysis of the following examples, which are not intended to be limiting in any way and are designed to further explain the invention.

EXAMPLES

Exemplary Losses in Film Manufacturing

Traditional film manufacturing results in a high amount of wasted components. Wasted components may arise as a result of scrap due to mixing, scrap lost in an oven, scrap lost due to slitting, and lost due to scrap. The below Exemplary Table shows how typical film manufacturing can result in a high amount of wasted material, including active.

EXEMPLARY TABLE

| Loss Due To Typical Manufacturing | | |
|---|---|---|
| | 115 kg batch | 380 kg batch |
| Theoretical Number Of Strips Desired | 460,000 | 1,520,000 |
| Strips To Coater | 422,693 | 1,466,423 |
| Mixing Scrap Loss | 8.1% | 3.5% |
| Strips Put In Slitter | 359,155 | 1,344,932 |
| Oven Scrap Loss | 13.8% | 8.0% |
| Strips To Packaging | 344,761 | 1,311,369 |
| Slitting Scrap Loss | 3.1% | 2.2% |
| Total Packaged Strips | 317,761 | 1,219,331 |
| Pouching Scrap Loss | 5.9% | 6.1% |
| Total Scrap Loss | 31% | 20% |

This exemplary amount of wasted material is based on the formation of a continuous film or sheet, which must be individually cut to form film strips and then transferred to a separate package. The above table is based on the process of making a coated sheet of film, using an example sheet that is about 75 cm wide and several hundred meters in length. Mixing Scrap Loss occurs at the mixer, Oven Scrap Loss occurs due to changing oven parameters to correct coat weight and moisture levels. Slitting Scrap Loss occurs due to the trimming of the sides of the film, and is typically between about 3% to about 12% loss. Packaging Scrap Loss (or Pouching Scrap Loss) includes additional edge trim, and includes the loss due to starting up a packaging machine and transferring the film to the packaging machine.

Because of the losses described above, there may be potentially huge economic incentives to develop more efficient production, and reduce the amount of materials lost during processing and packaging. It is estimated that the present invention may reduce the amount of wasted material by up to 75%.

Example 1

Coating of a PEO/HPMC Based Film on Packaging Foil

This Example was conducted to demonstrate the feasibility of coating a typical film solution onto packaging foil. A film forming solution was prepared, the solution including PEO/HPMC as the polymers, and including 30% solids content. The film forming matrix was made with the components of Table 1:

TABLE 1

| Component | Amount (Wt %) |
|---|---|
| Polyethylene Oxide WSR N10 LEO | 29.55 g (49.25%) |
| HPMC E15 | 14.778 g (24.63%) |
| polyol syrup | 7.386 g (12.31%) solids and 2.462 g water |
| Glycerin | 7.386 g (12.31%) |
| Glycerol Monooleate | 0.30 g (0.50%) |
| Titanium Dioxide | 0.60 g (1.00%) |
| Distilled Water | 137.538 g |

The polyol syrup, glycerin, glycerol monooleate, titanium dioxide and water were added to a fabricated glass bowl and mixed. Then a blend of PEO and HPMC was added to the bowl and mixed. The solution was prepared as described below using the Degussa Dental Multivac Compact. The solution was stirred for 40 minutes at 125 rmp in a 60% vacuum. The solution was then stirred for 40 minutes at 125 rpm in a 90% vacuum. The solution was then stirred for 12 minutes at 100 rpm in a 95% vacuum, and then stirred for 8 minutes at 100 rpm in a 98% vacuum. Distilled water was then added to obtain QS, and then the solution was stirred for 8 minutes at 100 rpm in a 100% vacuum.

The solution was then cast into a plurality of wet film forming products using a K-Control Coater (R K Print Coat Instruments Ltd.) with the micrometer adjustable wedge bar set at 450 microns onto both the product and non product side of packaging foil substrates and a paper substrate. The wet films were dried for 22 minutes in an 80° C. convection air oven. The results are as follows.

For films deposited onto the non product side of Alcan 15291, an Oriented Polyamide substrate, there was seen no edge creep (indicating optimal wetting between the liquid and the substrate, i.e., about a 90 degree contact angle), however, removal of the dried film from the substrate resulted in cohesive failure of the film when tested both immediately after drying and after two hours.

For films deposited onto the product side of Alcan 15291, a polypropylene based substrate, there was seen no edge creep (indicating optimum wetting between the liquid and the substrate), and the film released from the substrate without cohesive failure of the film both immediately after drying was complete and after cooling for two hours.

For films deposited onto the non product side of Alcan 90489, a polyethylene terephthalate based substrate, there was seen no edge creep, and the film released from the substrate without cohesive failure both immediately after drying was complete and after cooling for two hours.

For films deposited onto the product side of Alcan 90489, a polyethylene terephthalate based substrate, there was seen no edge creep, and the film released from the substrate without cohesive failure both immediately after drying was complete and after cooling for two hours.

For films deposited onto the non product side of Alcan 15288, an Oriented Polyamide substrate, there was seen no edge creep, and the film released from the substrate without cohesive failure both immediately after drying was complete and after cooling for two hours.

For films deposited onto the product side of Alcan 90489, a PVC based substrate, there was seen no edge creep, however removal of the film from the substrate resulted in cohesive failure of the film both immediately after drying and after cooling for two hours.

For films deposited onto RFE-042 foil (Amcor), there was seen no edge creep, however removal of the film from the substrate resulted in cohesive failure of the film both immediately after drying and after cooling for two hours.

For films deposited onto LCP-451 foil (Amcor), there was seen no edge creep, however removal of the film from the substrate resulted in cohesive failure of the film both immediately after drying and after cooling for two hours.

For films deposited onto the glossy HDPE side of 6330L paper (Loparex), there was noticeable edge creep (indicating excessive wetting between the liquid and the substrate), and the film had very little adhesion to the substrate immediately when drying was complete. This substrate was deemed unacceptable due to the lack of tight adhesion of the film to the substrate.

The results of this experiment demonstrate that the proper substrate material must be considered in light of the particular films being prepared. The goal is to provide a film that adheres sufficiently to the substrate surface without creep, but can be easily removed after drying is complete. Tightly bound substrates would probably not be useful since the film would tear when removing from these substrates (i.e., cohesive failure). The films had no noticeable edge creep in all cases except when using the paper substrate coated with polyolefin, which indicates optimum wetting properties in all cases except when using a paper substrate coated with polyolefin. These results indicate that it would be feasible to coat film strips onto specified packaging foil to eliminate the losses that are encountered during edge trimming in the packaging process.

Example 2

Use of Xylitol as Amorphous to Crystalline Excipient

The goal of this example was to investigate the adhesion of PEO/xylitol based film containing dextromethorphan on packaging foil substrates. A film forming solution was prepared, the solution including PEO/HPMC as the polymers, and including 30% solids content. The film forming matrix was made with the components of Table 2:

TABLE 2

| Component | Amount (Wt %) |
| --- | --- |
| Polyethylene Oxide WSR N80 LEO | 25.539 g (31.53%) |
| Xylitol | 17.026 g (21.02%) |
| Sucralose | 2.025 g (2.50%) |
| Magnasweet | 0.405 g (0.50%) |
| Sodium bicarbonate | 0.810 g (1.00%) |
| Dextramethorphan HBr | 25.313 g (31.25%) |
| Butylated hydroxytoluene | 0.081 g (0.10%) |
| Flavors | 8.810 g (11.00%) |
| Menthol | 0.810 g (1.00%) |
| Colorants | 0.081 g (0.10%) |
| Distilled Water | 99.000 g |

The menthol, colorants and water were added to a fabricated glass bowl and mixed. Then a blend of PEO, sucralose, magnasweet and sodium bicarbonate was added to the bowl and mixed. The solution was prepared as described below using the Degussa Multivac Compact. The solution was stirred for 20 minutes at 100 rpm in a 60% vacuum. The solution was then stirred for 20 minutes at 100 rpm in a 90% vacuum. The solution was then stirred for 4 minutes at 100 rpm in a 95% vacuum, and then stirred for 4 minutes at 100 rpm in a 100% vacuum. Distilled water was then added to obtain QS, and then the solution was stirred for 8 minutes at 100 rpm in a 100% vacuum. The xylitol was then added to the bowl, and the solution was stirred for 20 minutes at 100 rpm in a 100% vacuum. A solution of butylated hydroxytoluene and flavors were then added, and the mixture was stirred for 4 minutes at 125 rpm in a 100% vacuum. Finally, Dextramethorphan was added, and the solution was stirred for 4 minutes at 125 rpm in a 100% vacuum.

The solution was cast into a plurality of film forming products using the K-Control Coater (R K Print Coat Instruments Ltd.) with the micrometer adjustable wedge bar set at 365 microns onto different sides of various packaging foil substrates and a paper substrate. The films were dried for 18 minutes in an 80° C. convection air oven (XWR). The films were monitored immediately after removing from a drying oven, then after standing for 17 hours at room temperature, and finally after standing at room temperature for 114 hours. The results are described in Table 3 below.

TABLE 3

| Substrate Description | Status Initially After Removing From the Oven | Status After Standing at R.T. for 17 hours | Status After Standing at R.T. for 114 hours |
| --- | --- | --- | --- |
| Non Glossy Side HDPE Side of 6330L Paper Substrate | Film had slight edge creep, but released easily from substrate | Not Applicable | Not Applicable |
| Alcan 15288 (Non Product Side) (oPA) | Film had no edge creep, but would not release without deforming | Film would not release without deforming | Film would not release without deforming |
| Alcan 15288 (Product Side) (PVC) | Film had no edge creep, but would not release from substrate | Film would not release without deforming | Film would not release without deforming |
| Alcan 90489 (Product Side) (PET) | Film had no edge creep, but would not release from substrate | Film had less adhesion than initially but would not release without deforming | Film released from the substrate without deformation |

These results show that the adhesive strength of the dried film is too great initially out of the oven on tested foil substrates to remove without cohesive failure of the film, however, the adhesive strength of the dried film out of the oven was low on the tested paper substrate and the dried film removed without cohesive failure. After standing for 114 hours, the adhesive strength of the dried film was seen to be too great on oPA and PVC products (Non Product and Product Side of Alcan 15288) to remove without cohesive failure of the film. After standing for 114 hours, the adhesive strength of the dried film was seen to be low enough to remove from a PET substrate (Product Side of Alcan 90489) without cohesive failure of the film.

Example 3

Storage of a PEO/HPMC Based Film in a Cooled Environment on a Packaging Foil

The purpose of this example was to investigate the adhesion of PEO/HPMC based film on packaging foil after 24 hr storage in a cooled environment (at about −3° F.). A film forming matrix at 24% solids was prepared pursuant to the materials set forth in Table 4 below:

TABLE 4

| Component | Amount (g) (WT %) |
|---|---|
| WSR-N80 PEO | 44.80 (56.00%) |
| HPMC | 16.00 (20.00%) |
| Polydextrose | 16.00 (20.00%) |
| Glycerol Monooleate | 0.80 (1.00%) |
| Sucralose | 0.80 (1.00%) |
| Flavor | 0.80 (1.00%) |
| Titanium Dioxide | 0.80 (1.00%) |

The solution was prepared as described herein using a Heidolph RZR 2102 mixer for mixing and a Degussa Multivac Compact vacuum mixer for degassing. Glycerol Monooleate and Titanium Dioxide were added to a beaker that contained 152 g of distilled water. The solution was stirred at 200-350 rpm using the Heidolph RZR 2102 mixer. HPMC, PEO, Polydextrose, and Sucralose were then added to the solution, and the solution was stirred at 300-800 rpm until excipients were dispersed evenly. The solution was then stirred at 200-300 rpm for 1 hour. The flavor was then added, and the solution was stirred at 300-800 rpm for about 5 minutes. The solution was then stirred at 45-125 rpm for 1 hour. The resulting solution was then transferred to a Degussa Multivac Compact vacuum mixer and fully degassed (125 rpm stirring, 100% vacuum).

The solution was cast into a plurality of film forming products using the K-Control Coater (R K Print Coat Instruments Ltd.) with the micrometer adjustable wedge bar that was placed onto the packaging foil (substrate). The films were dried for 12 minutes in an 80° C. convection oven. The films were then sealed into a foil bag and placed into a –3° F. environment for 24 hours, and were then evaluated.

It was determined that there was no edge creep during the coating/drying process. Notably, the film release at room temperature was tight and could not release effectively. The films did not fully release from the substrate while in the –3° F. environment; however, subjectively, the films released easier than they did prior to being placed into the cold environment. The results of this test demonstrate that films maintained in a cooled environment may release easier than prior to storage in the cooled environment.

Example 4

Storage of HPMC/PEO/PEG Based Film in a Cooled Environment on a Packaging Foil

The purpose of this example was to investigate the adhesion of HPMC/PEO/PEG based film on packaging foil after 24 hr storage at cooled temperatures (about –3° F.). A film forming matrix at 24% solids was prepared pursuant to the materials set forth in Table 5 below:

TABLE 5

| Component | Amount (g) (WT %) |
|---|---|
| HPMC | 19.20 (40.00%) |
| WSR-N80 PEO | 17.28 (36.00%) |
| Polydextrose | 4.80 (10.00%) |
| PEG 600 | 4.80 (10.00%) |
| Glycerol Monooleate | 0.48 (1.00%) |
| Sucralose | 0.48 (1.00%) |
| Flavor | 0.48 (1.00%) |
| Titanium Dioxide | 0.48 (1.00%) |

The solution was prepared as described herein using a Heidolph RZR 2102 mixer for mixing and a Degussa Multivac Compact vacuum mixer for degassing. Glycerol Monooleate, PEG and Titanium Dioxide were added to a beaker that contained 152 g of distilled water. The solution was stirred at 200-350 rpm using the Heidolph RZR 2102 mixer. Methocel, WSR-N80 PEO, Polydextrose, and Sucralose were then added to the mixture, and the solution was stirred at 300-800 rpm until excipients were dispersed evenly. The solution was then stirred at 200-300 rpm for 1 hour. Flavor was then added and the solution was stirred at 300-800 rpm for ~5 minutes. The solution was then stirred at 45-125 rpm for 1 hour. The solution was then transferred to Degussa Multivac Compact vacuum mixer to fully degas the solution (125 rpm stirring, 100% vacuum).

The solution was cast into a plurality of film forming products using the K-Control Coater (R K Print Coat Instruments Ltd.) with the micrometer adjustable wedge bar that was placed onto the surface of RFE-042 packaging foil (Amcor). The films were dried for 12 minutes in an 80° C. convection oven.

It was determined that there was no edge creep during the coating/drying process. However, the film release at room temperature was slightly tight. The films did not fully release from the substrate while in the –3° F. environment; however, subjectively the films released easier than they did prior to being placed into the cold environment.

This experiment suggests that the polymer system does not reach the glassy state (below the Tg) when placed into the cooled environment (below zero degrees F.), and therefore a colder temperature is recommended, thus allowing the adhesion properties of the film to lessen and allow for easier removal. The ease of removal was found to be true even after the film was brought back up to room temperature, which demonstrates the effectiveness of temporarily storing the film in a cooled environment.

Example 5

Demonstrating the Effect of an Active and Polymer Composition Upon Adhesion and Release from a Packaging Substrate The purpose of this experiment was to investigate the adhesiveness of an active containing film formulation with different levels of PEO, in comparison with an active-containing formulation without PEO and a formulation without an active. In this experiment, the active used was Montelukast sodium (a leukotriene receptor antagonist). The compositions of the four comparative formulations investigated are shown below in Table 6.

TABLE 6

| Component | Batch A (Wt % of solids) | Batch B (Wt % of solids) | Batch C (Wt % of solids) | Batch D (Wt % of solids) |
|---|---|---|---|---|
| Montelukast Na | 27.03 | 30.47 | 34.91 | — |
| PEO N-10 | 22.58 | 12.72 | — | 30.95 |

TABLE 6-continued

| Component | Batch A (Wt % of solids) | Batch B (Wt % of solids) | Batch C (Wt % of solids) | Batch D (Wt % of solids) |
|---|---|---|---|---|
| HPMC (40-60 cps) | 20.32 | 22.91 | 26.25 | 27.85 |
| HPMC (4-6 cps) | 20.32 | 22.91 | 26.25 | 27.85 |
| Flavor(s) | 9.10 | 10.26 | 11.74 | 12.47 |
| glycerol monooleate | 0.65 | 0.73 | 0.84 | 0.89 |

All the above mentioned formulations included 112.50 g of water and were mixed using the Heidolph mixer. At the completion of the mixing step, all formulations were degassed using the Degussa multi-vac.

Batches A and B were mixed in the following manner: the HPMC (40-60 cps), HPMC (4-6 cps) and PEO N-10 were mixed with the water and stirred for at least 30 minutes. Flavors and GMO were then separately mixed with each other and allowed to sit until the initial mixing step was completed. The flavor solution was then added to the polymer solution, and the composition was mixed for at least 5 minutes. The active was then added to the mixture, and the composition was mixed for at least 30 minutes. The solution was then degassed.

Batch C was mixed in the following manner: the HPMC (40-60 cps) and HPMC (4-6 cps) were added to the water and mixed for at least 30 minutes. Flavors and GMO were then separately mixed with each other and allowed to sit until the initial mixing step was completed. The flavor solution was then added to the polymer solution, and the composition was mixed for at least 5 minutes. The active was then added to the mixture, and the composition was mixed for at least 30 minutes. The solution was then degassed.

Batch D was mixed in the following manner: the HPMC (40-60 cps), HPMC (4-6 cps) and PEO N-10 were mixed with the water and stirred for at least 30 minutes. Flavors and GMO were then separately mixed with each other and allowed to sit until the initial mixing step was completed. The flavor solution was then added to the polymer solution, and the composition was mixed for at least 5 minutes. The solution was then degassed.

Figure 4:
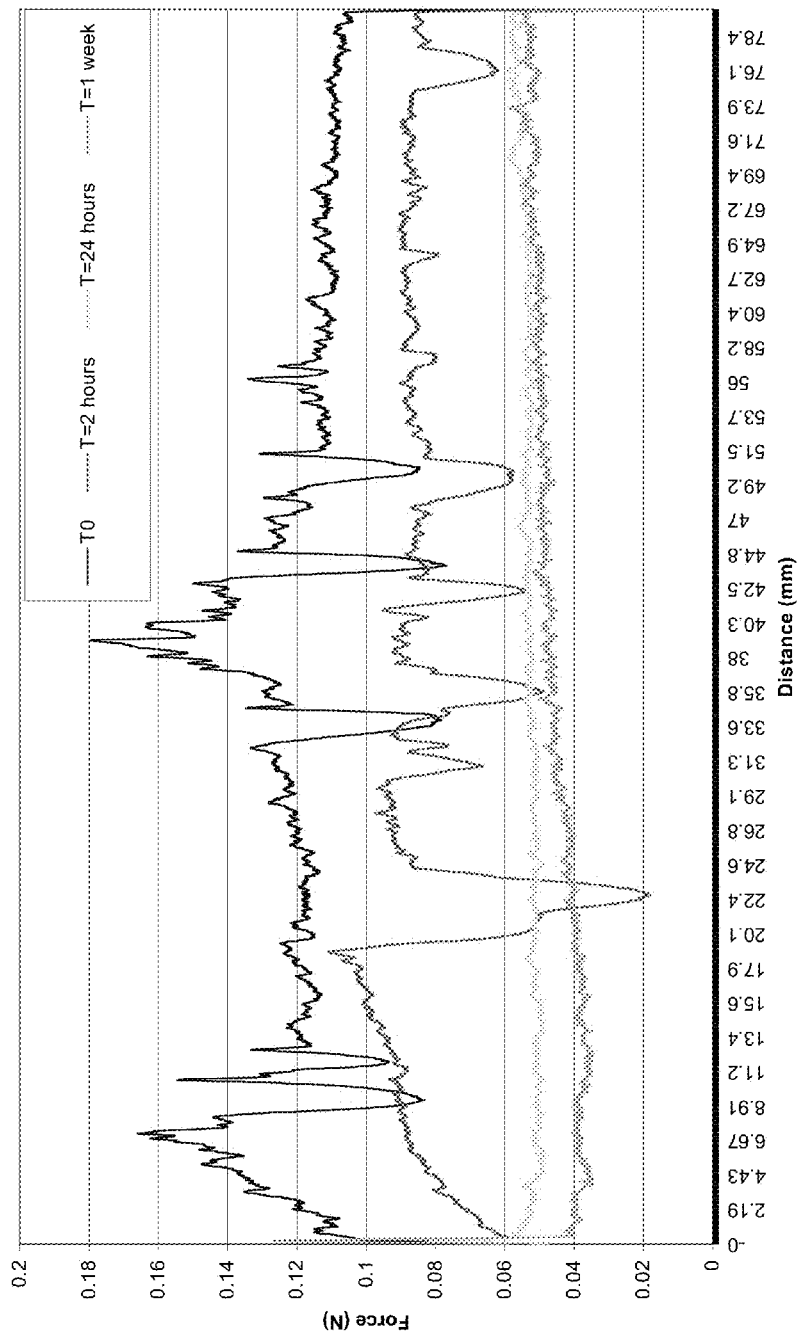
FIG. 4 is a graphical depiction of the results of the peel test of the Examples herein.
Figure 5:
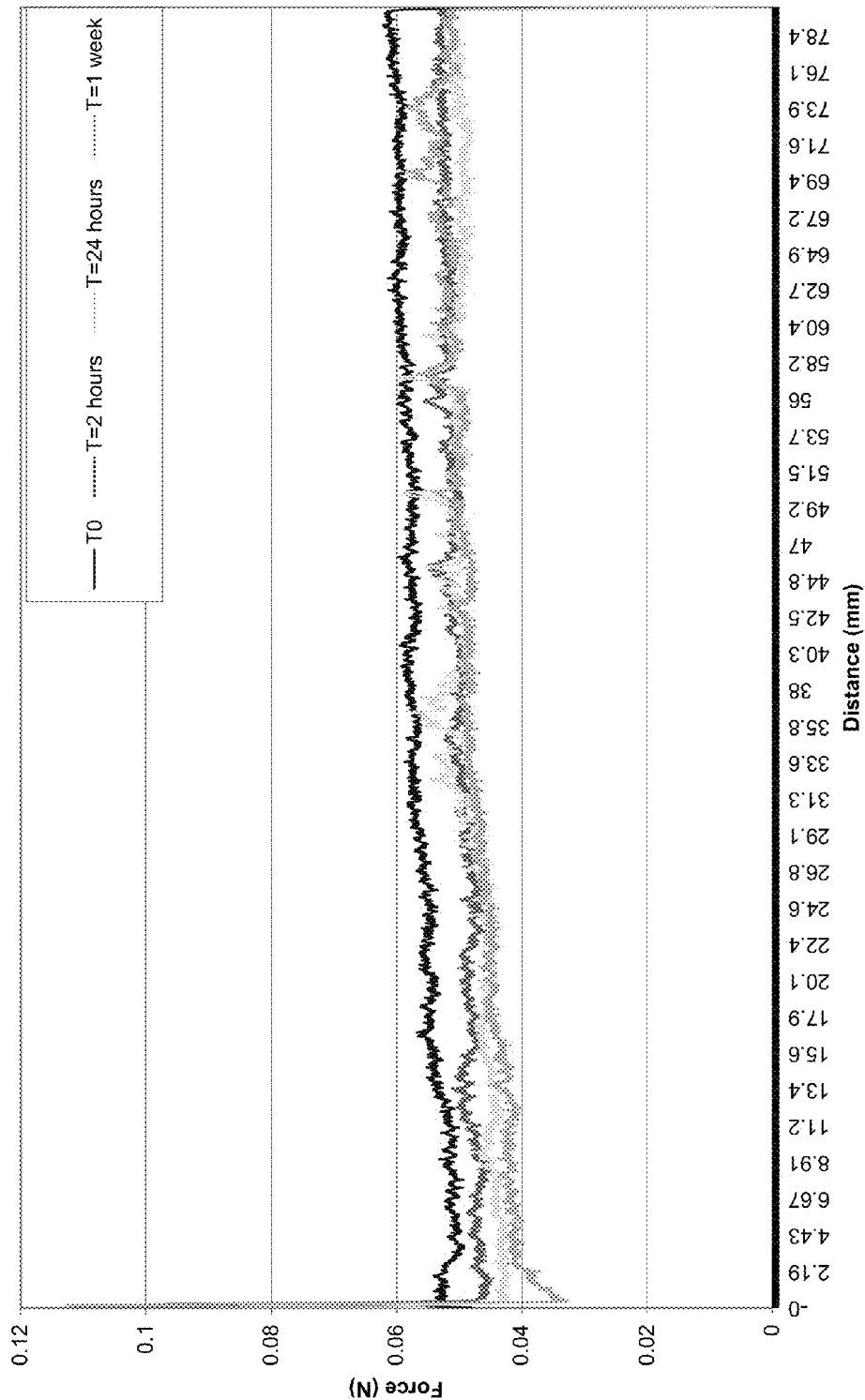
FIG. 5 is a graphical depiction of the results of the peel test of the Examples herein.
Figure 6:
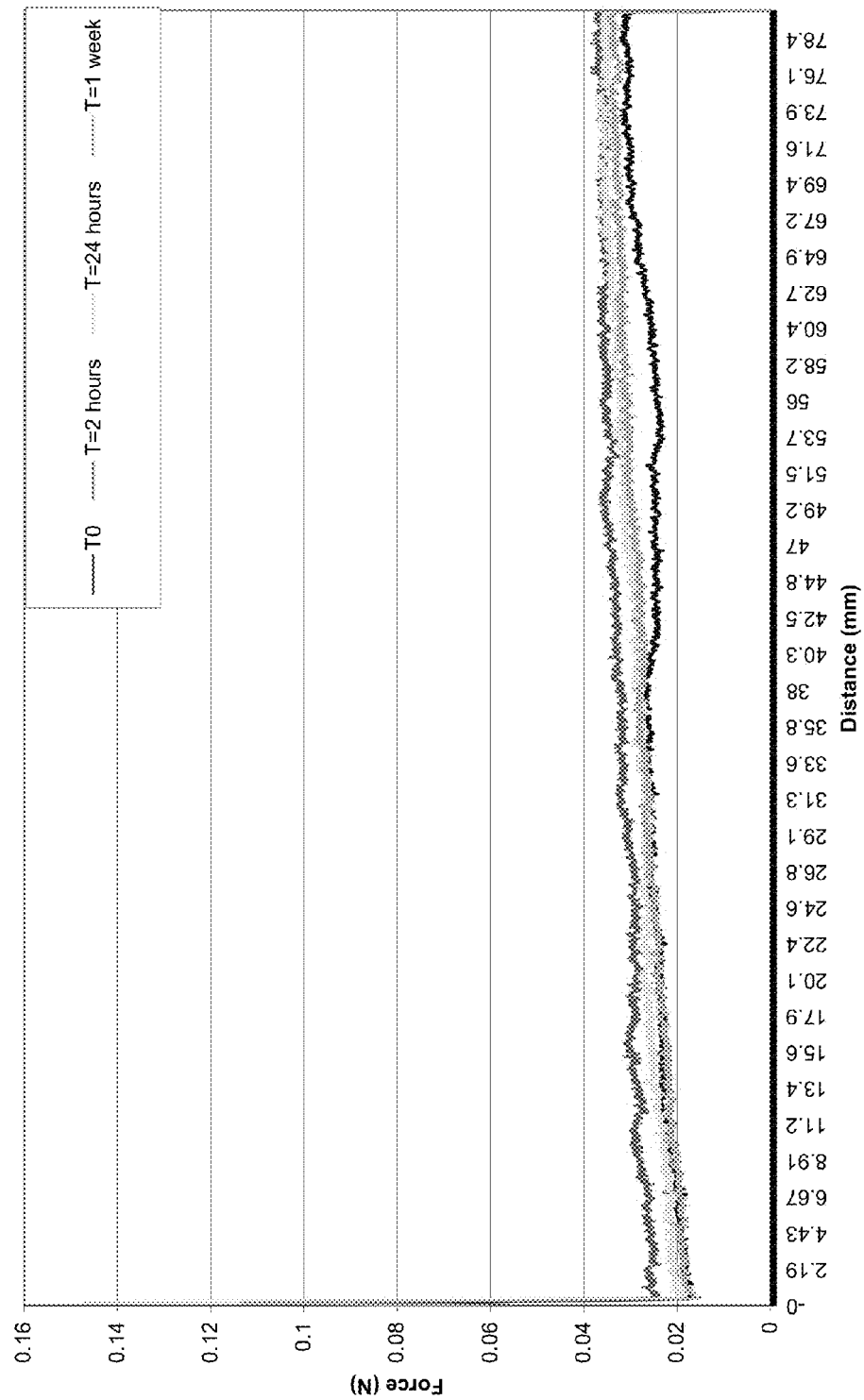
FIG. 6 is a graphical depiction of the results of the peel test of the Examples herein.
Figure 7:
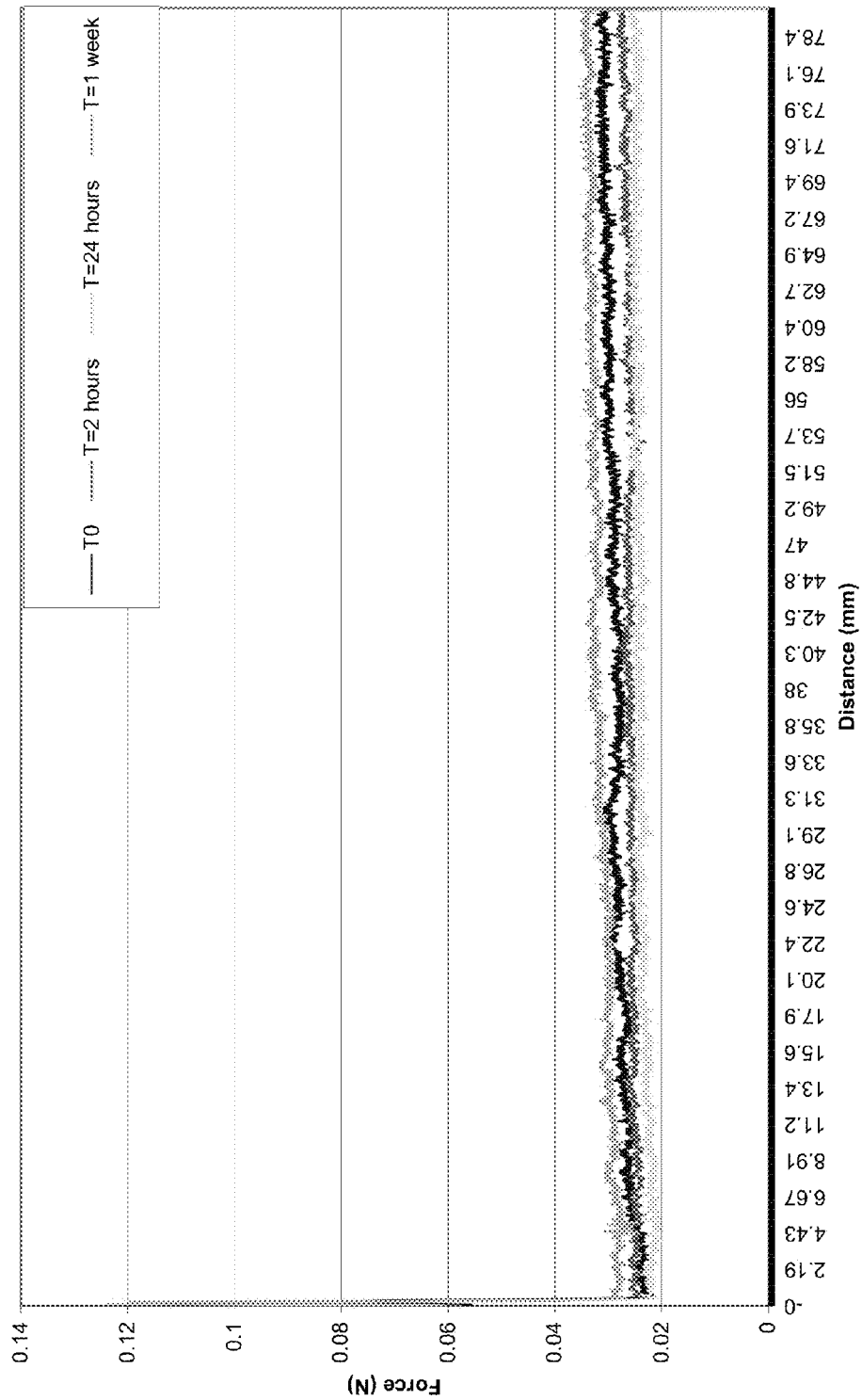
FIG. 7 is a graphical depiction of the results of the peel test of the Examples herein.
Figure 8:
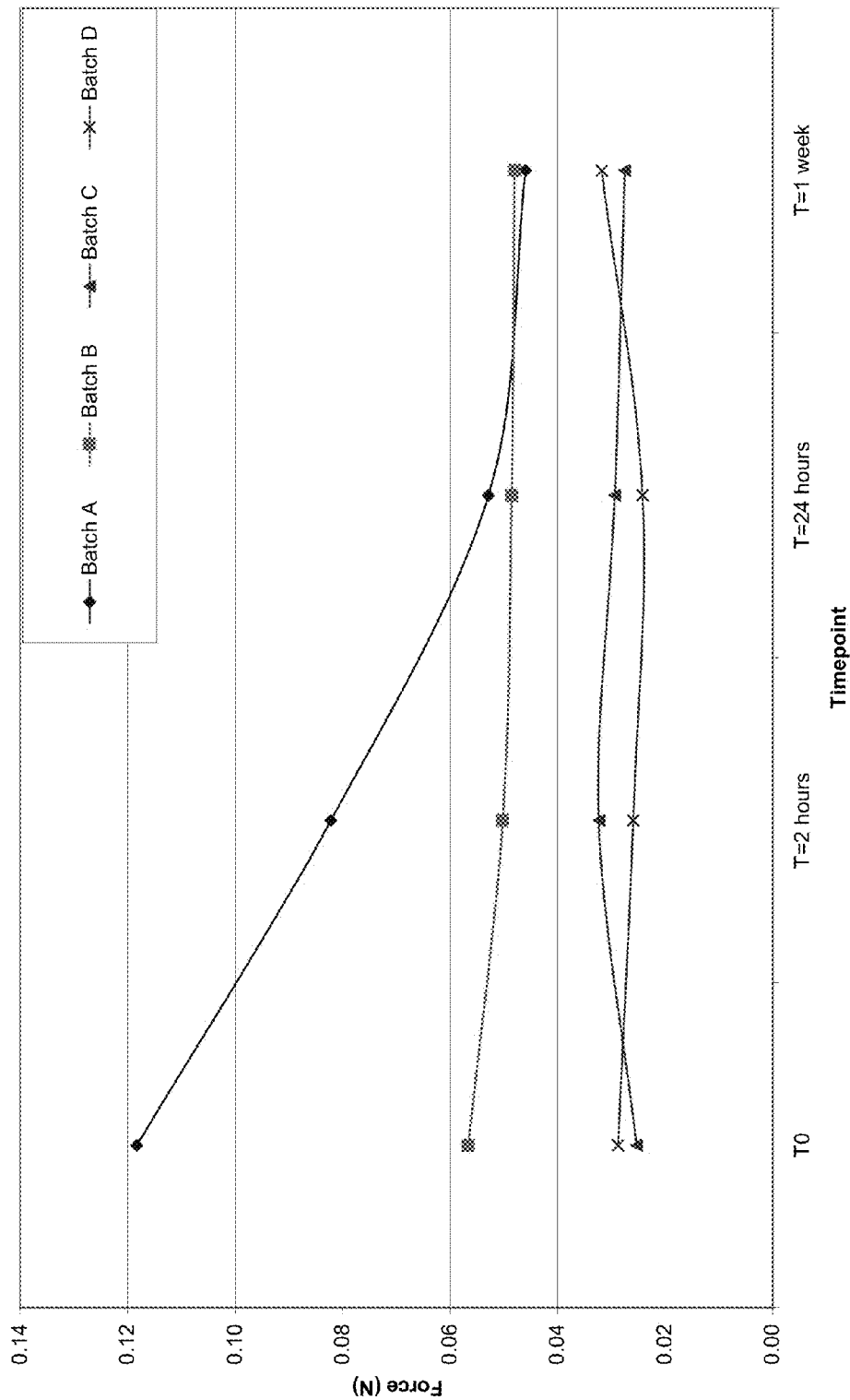
FIG. 8 is a comparative table depicting the results of the peel test of the Examples herein.

After the mixing steps were completed, the formulations were then coated on a Dupont A untreated PET substrate using a K-coater. All films were dried at 90° C. for 10 minutes in a convection oven. After drying, films strips were cut out of the bulk film to ensure that the individual strip weight was within ±3% of the target strip weight. The remaining bulk films were then subjected to peel testing to determine the adhesiveness of the film to the substrate. Peel testing is a measure of the ease of removal of the film from the substrate by the consumer. Any hysteresis seen in the data indicates a deformation (such as a stretching) of the film, and is therefore considered a failure. Peel testing was performed at the following intervals: immediately after dry, 2 hours after dry, 24 hours after dry and 1 week after dry. The results from these tests are shown in the graphs of FIGS. 4-8. The top line on FIG. 4 is at zero time, the second from the top is at 2 hours, the third from the top is at 24 hours and the bottom line is at 1 week. FIG. 8 shows a summary of the results of FIGS. 4-7 over the various time periods.

As can be seen, the adhesion was found to be strongest when the PEO and Montelukast Sodium were combined. Further, the results show that the level of adhesiveness can be changed by adjusting the amount of PEO in the formulation. Because the level of PEO can alter adhesiveness, it may be said that changing the amount of Montelukast in the formulation may alter the adhesiveness. The change in adhesiveness could be due to the interaction between the amorphous state of the Montelukast and the amorphous phase of the polymer.

This experiment provides evidence that control of the adhesiveness of the polymer to the substrate is achieved either by polymer selection and/or by interaction of an active with the polymer. The experiment also provides evidence that even very tacky films such as Batch A can easily release from the substrate if given enough time. Notice that after 24 hours, the force required for the removal of the film in Batch A approaches 0.06 N which is very similar to Batch B, which released from the substrate smoothly without the hysteresis seen in Batch A. Since hysteresis in this test indicates a deformation of the active film, no hysteresis is preferred.

What is claimed is:

1. A method of forming an individual film dosage, comprising the steps of:
    a. Preparing a film forming matrix;
    b. Providing a substantially flat packaging material substrate having a top surface;
    c. Depositing a plurality of pre-determined amounts of said matrix onto said top surface of said packaging material substrate to form a plurality of wet film forming products;
    d. Drying said plurality of wet film forming products to form a plurality of dried film products removably adhered to said packaging material substrate; and
    e. Placing a sealing layer on said top surface of said packaging material substrate, wherein said sealing layer effectively seals the plurality of dried film products between the sealing layer and the packaging material substrate to form a package.

2. The method of claim 1, wherein said film forming matrix includes at least one water soluble polymer.

3. The method of claim 1, wherein said pre-determined amount of said matrix comprises a sufficient level of active material to provide one dosage of said active material.

4. The method of claim 1, wherein said packaging material substrate comprises a material selected from the group consisting of foil, plastic, mylar, and combinations thereof.

5. The method of claim 1, wherein said sealing material comprises a material selected from the group consisting of foil, plastic, mylar, and combinations thereof.

6. The method of claim 1, wherein said step of depositing is achieved via off-set printing.

7. The method of claim 1, wherein said step of depositing is achieved via direct printing.

8. The method of claim 1, wherein said step of depositing is achieved via start-and-stop slot die coating.

9. The method of claim 1, wherein each of said plurality of wet film forming products is substantially square shaped.

10. The method of claim 1, wherein said plurality of wet film forming products is substantially rectangular shaped.

11. The method of claim 1, wherein said plurality of dried film products is stored for a desired period of time prior to the step (e) of placing a sealing layer on said top surface.

12. The method of claim 1, wherein said plurality of wet film forming products is deposited onto the top surface such that at least a portion of said top surface is exposed around the periphery of each of the deposited plurality of wet film forming products.

13. The method of claim 12, wherein the sealing layer is adhered to the top surface of the packaging material substrate at said periphery.

14. The method of claim 13, wherein said sealing layer is adhered to the top surface of the packaging material substrate via a method selected from the group consisting of heat laminating, chemical laminating, radiation, ultrasonic welding, compression, adhesive bonding, and combinations thereof.

15. The method of claim 13, wherein adhering said sealing layer to the top surface of the packaging material substrate forms a compartment, said compartment comprising said dried film product.

16. The method of claim 12, wherein about 2 to about 30 individual wet film forming products are deposited on said top surface in a substantially side-by-side manner along the width of the top surface.

17. The method of claim 1, further comprising the step (f) of cutting said packaging material substrate and sealing layer to provide an individual sealed product.

18. The method of claim 1, wherein said film forming matrix comprises a crystallization promoter.

19. The method of claim 18, wherein said crystallization promoter comprises a sugar alcohol.

20. The method of claim 1, wherein after the step (e) of depositing a sealing layer on said top surface, the dried film product is stored at a cool temperature.

21. The method of claim 1, wherein said individual dosage form comprises at least one active.

22. The method of claim 21, wherein said film forming matrix comprises said at least one active.

23. The method of claim 21, further comprising the step of adding said at least one active to at least one of said plurality of wet film forming products prior to drying.

24. The method of claim 23, wherein said adding of said at least one active comprises controllably metering and disposing said at least one active on a surface of said at least one of said plurality of wet film forming products.

25. The method of claim 23, wherein said adding of said at least one active comprises:
 a. use of a doctor blade to add said at least one active on a surface of said at least one of said plurality of wet film forming products;
 b. use of a roller to add said at least one active on a surface of said at least one of said plurality of wet film forming products;
 c. spraying said at least one active on a surface of said at least one of said plurality of wet film forming products;
 d. depositing said at least one active on a surface of said at least one of said plurality of wet film forming products;
 e. use of simple or dual slot die extrusion to add said at least one active on a surface of said at least one of said plurality of wet film forming products;
 f. or a combination thereof.

26. The method of claim 23, wherein said adding of said at least one active is in the form of active-containing particles and said active containing particles are securably disposed onto the film.

27. The method of claim 26, wherein said active containing particles are partially embedded in or partially encased by said film products.

28. The method of claim 21, further comprising the step of adding said at least one active to said plurality of dried film forming products.

29. The method of claim 28, wherein said adding of said at least one active comprises controllably metering and disposing said at least one active on a surface of said at least one of said plurality of dried film forming products.

30. The method of claim 28, wherein said adding of said at least one active comprises:
 a. use of a doctor blade to add said at least one active on a surface of said at least one of said plurality of dried film forming products;
 b. use of a roller to add said at least one active on a surface of said at least one of said plurality of dried film forming products;
 c. spraying said at least one active on a surface of said at least one of said plurality of dried film forming products;
 d. depositing said at least one active on a surface of said at least one of said plurality of dried film forming products;
 e. use of simple or dual slot die extrusion to add said at least one active on a surface of said at least one of said plurality of dried film forming products;
 f. or a combination thereof.

31. The method of claim 28, wherein said adding of said at least one active is in the form of active-containing particles and said active-containing particles are securably disposed onto a surface of said at least one of said plurality of dried film forming products.

32. The method of claim 31, wherein said active containing particles are partially embedded in or partially encased by said film.

33. The method of claim 21, wherein said film forming matrix comprises said at least one first active and the method further comprises the step of adding said at least one second active to at least one of said plurality of wet film forming products prior to drying.

34. The method of claim 33, wherein said adding of said at least one second active comprises controllably metering and disposing said at least one second active on a surface of said at least one of said plurality of wet film forming products.

35. The method of claim 33, wherein said adding of said at least one second active comprises:
 a. use of a doctor blade to add said at least one second active on a surface of said at least one of said plurality of wet film forming products;
 b. use of a roller to add said at least one second active on a surface of said at least one of said plurality of wet film forming products;
 c. spraying said at least one second active on a surface of said at least one of said plurality of wet film forming products;
 d. depositing said at least one second active on a surface of said at least one of said plurality of wet film forming products;
 e. use of simple or dual slot die extrusion to add said at least one second active on a surface of said at least one of said plurality of wet film forming products;
 f. or a combination thereof.

36. The method of claim 33, wherein said adding of said at least one second active is in the form of active-containing particles and said active containing particles are securably disposed onto the film.

37. The method of claim 36, wherein said active containing particles are partially embedded in or partially encased by said film products.

38. The method of claim 21, wherein said film forming matrix comprises said at least one first active and the method further comprises the step of adding said at least one second active to said plurality of dried film forming products.

39. The method of claim 38, wherein said adding of said at least one second active comprises controllably metering and disposing said at least one second active on a surface of said at least one of said plurality of dried film forming products.

40. The method of claim 38, wherein said adding of said at least one second active comprises:
 a. use of a doctor blade to add said at least one second active on a surface of said at least one of said plurality of dried film forming products;

b. use of a roller to add said at least one second active on a surface of said at least one of said plurality of dried film forming products;
c. spraying said at least one second active on a surface of said at least one of said plurality of dried film forming products;
d. depositing said at least one second active on a surface of said at least one of said plurality of dried film forming products;
e. use of simple or dual slot die second extrusion to add said at least one active on a surface of said at least one of said plurality of dried film forming products;
f. or a combination thereof.

41. The method of claim 38, wherein said adding of said at least one second active is in the form of active-containing particles and said active-containing particles are securably disposed onto a surface of said at least one of said plurality of dried film forming products.

42. The method of claim 41, wherein said active containing particles are partially embedded in or partially encased by said film.

43. The method of claim 1, wherein each individual film dosage comprises a target weight of an active, and wherein the amount of said active in each individual film dosage does not vary more than 10% from said target weight of said active.

44. A method of forming an individual film dosage, comprising the steps of:
  a. Preparing a film forming matrix comprising at least one water soluble polymer;
  b. Providing a substantially flat packaging material substrate having at least one top surface;
  c. Depositing a plurality of pre-determined amounts of said film forming matrix onto said top surface of said packaging material substrate to form a plurality of wet film forming products;
  d. Drying said plurality of wet film forming products to form a plurality of dried film products removably adhered to said packaging material substrate;
  e. Storing said plurality of dried film products for a pre-determined length of time; and
  f. Placing a sealing layer on said top surface of said packaging material substrate, wherein said sealing layer effectively seals the plurality of dried film products between the sealing layer and the packaging material substrate to form a package.

45. The method of claim 44, wherein said step (e) of storing said dried film product comprises rolling said packaging material substrate with said dried film product thereon and storing said rolled packaging material substrate for said pre-determined length of time.

46. The method of claim 44, wherein said pre-determined amount of said matrix comprises a sufficient level of active material to provide one dosage of said active material.

47. The method of claim 44, wherein said packaging material substrate comprises a material selected from the group consisting of foil, plastic, mylar, and combinations thereof.

48. The method of claim 44, wherein said sealing material comprises a material selected from the group consisting of foil, plastic, mylar, and combinations thereof.

49. The method of claim 44, wherein said step of depositing is achieved via off-set printing.

50. The method of claim 44, wherein said step of depositing is achieved via direct printing.

51. The method of claim 44, wherein said step of depositing is achieved via start-and-stop slot die coating.

52. The method of claim 44, wherein each of said plurality of wet film forming products is substantially square shaped.

53. The method of claim 44, wherein each of said plurality of wet film forming products is substantially rectangular shaped.

54. The method of claim 44, wherein said plurality of wet film forming products is deposited onto the top surface such that at least a portion of said top surface is exposed around the periphery of each of the deposited plurality of wet film forming products.

55. The method of claim 54, wherein the sealing layer is adhered to the top surface of the packaging material substrate at said periphery.

56. The method of claim 55, wherein said sealing layer is adhered to the top surface of the packaging material substrate via a method selected from the group consisting of heat laminating, chemical laminating, radiation, ultrasonic welding, compression, adhesive bonding, and combinations thereof.

57. The method of claim 54, wherein adhering said sealing layer to the top surface of the packaging material substrate forms a compartment, said compartment comprising said dried film product.

58. The method of claim 54, wherein about 2 to about 30 individual wet film forming products are deposited on said top surface in a substantially side-by-side manner along the width of the top surface.

59. The method of claim 44, further comprising the step (g) of cutting said packaging material substrate and sealing layer to provide an individual sealed product.

60. The method of claim 44, wherein said film forming matrix comprises a crystallization promoter.

61. The method of claim 60, wherein said crystallization promoter comprises a sugar alcohol.

62. The method of claim 44, wherein after the step (f) of depositing a sealing layer on said top surface, the dried film product is stored at a cool temperature.

63. The method of claim 44, wherein prior to the step (f) of depositing a sealing layer on said top surface, the dried film product is stored at a cool temperature.

64. The method of claim 44, wherein said step of storing said dried film product for a pre-determined length of time comprises rolling said packaging material substrate and dried film with a release liner.

65. The method of claim 44, wherein said individual dosage form comprises at least one active.

66. The method of claim 65, wherein said film forming matrix comprises said at least one active.

67. The method of claim 65, further comprising the step of adding said at least one active to at least one of said plurality of wet film forming products prior to drying.

68. The method of claim 67, wherein said adding of said at least one active comprises controllably metering and disposing said at least one active on a surface of said at least one of said plurality of wet film forming products.

69. The method of claim 67, wherein said adding of said at least one active comprises:
  a. use of a doctor blade to add said at least one active on a surface of said at least one of said plurality of wet film forming products;
  b. use of a roller to add said at least one active on a surface of said at least one of said plurality of wet film forming products;
  c. spraying said at least one active on a surface of said at least one of said plurality of wet film forming products;
  d. depositing said at least one active on a surface of said at least one of said plurality of wet film forming products;
  e. use of simple or dual slot die extrusion to add said at least one active on a surface of said at least one of said plurality of wet film forming products;
  f. or a combination thereof.

70. The method of claim 67, wherein said adding of said at least one active is in the form of active-containing particles and said active containing particles are securably disposed onto the film.

71. The method of claim 70, wherein said active containing particles are partially embedded in or partially encased by said film products.

72. The method of claim 65, further comprising the step of adding said at least one active to said plurality of dried film forming products.

73. The method of claim 72, wherein said adding of said at least one active comprises controllably metering and disposing said at least one active on a surface of said at least one of said plurality of dried film forming products.

74. The method of claim 72, wherein said adding of said at least one active comprises:
   a. use of a doctor blade to add said at least one active on a surface of said at least one of said plurality of dried film forming products;
   b. use of a roller to add said at least one active on a surface of said at least one of said plurality of dried film forming products;
   c. spraying said at least one active on a surface of said at least one of said plurality of dried film forming products;
   d. depositing said at least one active on a surface of said at least one of said plurality of dried film forming products;
   e. use of simple or dual slot die extrusion to add said at least one active on a surface of said at least one of said plurality of dried film forming products;
   f. or a combination thereof.

75. The method of claim 72, wherein said adding of said at least one active is in the form of active-containing particles and said active-containing particles are securably disposed onto a surface of said at least one of said plurality of dried film forming products.

76. The method of claim 75, wherein said active containing particles are partially embedded in or partially encased by said film.

77. The method of claim 65, wherein said film forming matrix comprises said at least one first active and the method further comprises the step of adding said at least one second active to at least one of said plurality of wet film forming products prior to drying.

78. The method of claim 77, wherein said adding of said at least one second active comprises controllably metering and disposing said at least one second active on a surface of said at least one of said plurality of wet film forming products.

79. The method of claim 77, wherein said adding of said at least one second active comprises:
   a. use of a doctor blade to add said at least one second active on a surface of said at least one of said plurality of wet film forming products;
   b. use of a roller to add said at least one second active on a surface of said at least one of said plurality of wet film forming products;
   c. spraying said at least one second active on a surface of said at least one of said plurality of wet film forming products;
   d. depositing said at least one second active on a surface of said at least one of said plurality of wet film forming products;
   e. use of simple or dual slot die extrusion to add said at least one second active on a surface of said at least one of said plurality of wet film forming products;
   f. or a combination thereof.

80. The method of claim 77, wherein said adding of said at least one second active is in the form of active-containing particles and said active containing particles are securably disposed onto the film.

81. The method of claim 80, wherein said active containing particles are partially embedded in or partially encased by said film products.

82. The method of claim 65, wherein said film forming matrix comprises said at least one first active and the method further comprises the step of adding said at least one second active to said plurality of dried film forming products.

83. The method of claim 82, wherein said adding of said at least one second active comprises controllably metering and disposing said at least one second active on a surface of said at least one of said plurality of dried film forming products.

84. The method of claim 82, wherein said adding of said at least one second active comprises:
   a. use of a doctor blade to add said at least one second active on a surface of said at least one of said plurality of dried film forming products;
   b. use of a roller to add said at least one second active on a surface of said at least one of said plurality of dried film forming products;
   c. spraying said at least one second active on a surface of said at least one of said plurality of dried film forming products;
   d. depositing said at least one second active on a surface of said at least one of said plurality of dried film forming products;
   e. use of simple or dual slot die second extrusion to add said at least one active on a surface of said at least one of said plurality of dried film forming products;
   f. or a combination thereof.

85. The method of claim 82, wherein said adding of said at least one second active is in the form of active-containing particles and said active-containing particles are securably disposed onto a surface of said at least one of said plurality of dried film forming products.

86. The method of claim 85, wherein said active containing particles are partially embedded in or partially encased by said film.

87. The method of claim 44, wherein each individual film dosage comprises a target weight of an active, and wherein the amount of said active in each individual film dosage does not vary more than 10% from said target weight of said active.

* * * * *